United States Patent [19]
Schmidt et al.

[11] Patent Number: 5,985,634
[45] Date of Patent: Nov. 16, 1999

[54] POLYPEPTIDES AND POLYNUCLEOTIDES RELATING TO THE α- AND β-SUBUNITS OF GLUTAMATE DEHYDROGENASES AND METHODS OF USE

[75] Inventors: Robert R. Schmidt, Gainesville, Fla.; Philip Miller, Ballwin, Mo.

[73] Assignee: University of Florida Research Foundation, Inc., Gainesville, Fla.

[21] Appl. No.: 08/828,451

[22] Filed: Mar. 28, 1997

Related U.S. Application Data

[62] Division of application No. 08/541,033, Oct. 6, 1995, Pat. No. 5,879,941.

[51] Int. Cl.$^6$ .............................. C12N 9/06; C12N 15/29; C12N 15/53; C12N 15/62
[52] U.S. Cl. ........................ 435/191; 435/69.7; 435/69.8; 530/370
[58] Field of Search ................................ 435/172.3, 69.7, 435/69.8, 191; 530/370

[56] References Cited

FOREIGN PATENT DOCUMENTS

WO 9509911  4/1995  WIPO.

OTHER PUBLICATIONS

Miller et al. Plant Mol. Biol. 0: 1–21, 1998.

Cock, J.M. et al. (1991) "A nuclear gene with many introns encoding ammonium–inducible chloroplastic NADP–specific glutamate dehydrogenase(s) in *Chlorella sorokiniana*" Plant Moledular Biology 17:1023–1044.

Bascomb, N.F. et al. (1987) "Different Rates of Synthesis and Degradation of Two Chloroplastic Ammonium–inducible NADP–Specific Glutamate Dehydrogenase Isoenzymes during Induction and Deinduction of *Chlorella sorokiniana* Cells" Plant Physiol. 83:85–91.

Bascomb, N.F., R. R. Schmidt (1987) "Purification and Partial Kinetic and Physical Characterization of Two Chloroplast–Localized NADP–Specific Glutamate Dehydrogenase Isoenzymes and Their Preferential Accumalation in *Chlorella sorokiniana* Cells Cultured at Low or High Ammonium Levels" Plant Physiol. 83:75–84.

Prunkard, D.E. et al. (1986) "Effect of Different Carbon Sources on the Ammonium Induction of Different Forms of NADP–Specific Glutamate Dehydrogenase in *Chlorella sorokiniana* Cells Cultured in the Light and Dark" Plant Physio. 81:413–422.

Yeung, A.T. et al. (1981) "Purification of an Ammonium–Inducible Glutamate Dehydrogenase and the Use of its Antigen Affinity Column–Purified Antibody in Specific Immunoprecipitation and Immunoadsorption Procedures" Analytical Biochemistry 110:216–228.

Meredith, M.J. et al. (1978) "Physical and Kinetic Properties of the Nicontinamide Adenine Dinucleotide–specific Glutamate Dehydrogenase Purified from *Chlorella sorokiniana*" Plant Physio. 61:967–974.

Srivastava, H.S., R. P. Singh (1987) "Role and Regulation of L–Glutamate Dehydrogenase Activity in Higher Plants" Phytochemistry 26(3):597–610.

Prunkard, D. E. et al. (1986) "Evidence for Chloroplastic Localization of an Ammonium–Inducible Glutamate Dehydrogenase and Synthesis of its Subunit from a Cytosolic Precursor–Protein in *Chlorella sorokiniana*" Plant Physio. 81:349–355.

Wallsgrove, R.M. et al. (1987) "Barley Mutants Lacking Chloroplast Glutamine Synthetase–Biochemical and Genetic Analysis" Plant Physio. 83:155–158.

Miflin, B.J. P. J. Lea (1979) "The Pathway of Nitrogen Assimilation in Plants" Phytochemistry 15:873–885.

"Niotinasmide Adenine Dl Nucleotide Glutamate Dehydrogenase Obtain Chlorella Cell Buffer Extract Two Stage Chromatography Phosphate Buffer Elution" (1982) Biochem. Inst., **abstract only.In.

Napoli et al. Introduction of a chimeric chalcone synthase gene into petunia results lin reversible co–suppression of homologous genes in trans. The Plant Cell. 2:279–289 (1990).

Bascomb, N.F. et al. (1986) "Specific Polysome Innunoadsorption to Purify an Ammonium–Inducible Glutamate Dehydrogenase MRNA from *Chlorella sorokiniana* and synthesis of Full Length Double–Stranded cDNA from the Purified MRNA" Plant Physio. 81:527–532.

Miller, P. W. et al. (1994) "Transcription initiation site of a NADP–specific glutamate dehydrogenase gene and potential use of its promoter region to express foreign genes in ammonium–cultured *Chlorella sorokiniana* cells" Journal of Applied Phycology 6:211–223.

Meredith, M. J. R.R. Schmidt (1991) "NAD–Specific glutamate dehydrogenase isoenzyme localized in mitochondria of nitrate–cultured *Chlorella sorokinian cells*" Plant Physio. 10:67–71.

*Primary Examiner*—David T. Fox
*Attorney, Agent, or Firm*—Saliwanchik, Lloyd & Saliwanchik

[57] ABSTRACT

Amino acid and nucelotide sequences relating to the glutamate dehydrogenase (GDH) enzyme are described. The GDH enzymes descnred herein were discovered in the alga *Chlorella sorokinina* in the form of seven different inducible isoenzymes. These isoenzymes are found in the algae as chloroplast-localized hexamers composed of α- and β-subunits. Plants transfromed with nucleotide sequences encoding the α- or β-subunits of the enzyme show imrpoved properties, for example, increased growth and improved stress tolerance.

15 Claims, No Drawings

POLYPEPTIDES AND POLYNUCLEOTIDES RELATING TO THE α- AND β-SUBUNITS OF GLUTAMATE DEHYDROGENASES AND METHODS OF USE

This is a division, of application Ser. No. 08/541,033, filed Oct. 6, 1995, now U.S. Pat. No. 5,879,941.

BACKGROUND OF THE INVENTION

Inorganic nitrogen acquired by plants is ultimately converted to ammonium before being assimilated in organic nitrogen metabolism. One enzyme postulated to be involved in the assimilatory process is glutamate dehydrogenase (GDH), a group of ubiquitous enzymes found to be present in almost all organisms from microbes to higher plants and animals (Srivastava, H. S., R. P. Singh [1987] *Phytochem.* 26:597–610). GDH catalyses the reversible conversion of α-ketoglutarate to glutamate via a reductive almnation that utilizes reduced β-nicotinamide adenine dinucleotide (NADH) or reduced β-nicotinamide adenine dinucleotide phosphate (NADPH) as a cofactor. The role of plant GDHs in the assimilation of ammonium into amino acids has been questioned since the discovery of the glutamine synthetase/glutamate synthase (GS/GOGAT) pathway that is believed to be the favored pathway for ammonium assimilation in higher plants (Miflin, B. J., P. J. Lea [1976] *Phytochem.* 15:873–885).

The primary objection to GDH playing a major role in plant nitrogen metabolism is its low afiniy for ammonium that would require high intracellular ammnonium concentrations to function anabolically. Early evidence indicated that GDH is a catabolic enzyme catalyzing the deamination of glutamate with only a partially anabolic function in synthesizing glutamate (Wallgrove, J. C., N. P. Hall, A. C. Kendall, [1987] *Plant Physiol.* 83:155–158). The physiological role of large amounts of GDH present in various plant tissues and organelles is still unclear, and possible conditions under which GDH may play a significant role in carbon and nitrogen metabolism have not been resolved.

The majority of plant GDHs characterized to date are localized in the mitochondria; however, a GDH species differing in several properties (i.e., cofactor specificity, $K_m$ values, organelle localization, thermal stability) has been characterized from the chloroplast of a unicellular green alga *Chlorella sorokiniana*. *C. sorokiniana* cells have been shown to possess a constitutive, mitochondrial, tetrameric NAD-specific GDH (Meredith, M. J., R. M. Gronostajski, R. R. Schmidt [1978] *Plant Physiol.* 61:967–974), and seven ammonium-inducible, chloroplast-localized, homo- and heterohexameric NADP-GDH isoenzymes (Prunkard, D. E., N. F. Bascomb, R. W. Robinson, R. R. Schmidt [1986] *Plant Physiol.* 81:349–355; Bascomb, N. E., R. R. Schmidt [1987] *Plant Physiol.* 83:75–84). The seven chloroplastic NADP-GDH isoenzymes were shown to have different electrophoretic mobilities during native-PAGE, and presumably result from the formation of homo- and heterohexamers composed of varying ratios of α- and β-subunits (53.5 and 52.3 kilodaltons, respectively).

Chlorefla cells cultured in 1 to 2 mM ammonium medium accumulate only the α-homohexamer (Bascomb and Schmidt, supra). The addition of higher ammonium concentrations (3.4 to 29 mM) to nitrate-cultured cells results in the accumulation of both α- and β-subunits in NADP-GDH holoenzymes (Prunkard et al., supra; Bascomb and Schmidt, supra; Bascomb, N. F., D. E. Prunkard, R. R. Schmidt [1987] *Plant Physiol.* 83:85–91). Prunkard et al. (Prunkard, D. E., N. F. Bascomb, N F, W. T. Molin, R. R. Schmidt [1986] *Plant Physiol.* 81:413–422) demonstrated that the NADP-GDH subunit ratio and isoenzyme pattern is influenced by both the carbon and nitrogen source as well as the lift conditions under which cells are cultured.

α- and β-NADP-GDH homohexamers purified from Chlorella cells have strikingly different ammonium $K_m$ values; however, the $K_m$ values for their other substrates are very similar. The α-homohexamer (composed of six identical α-subunits) that catalyzes the biosynthesis of glutamate is allosterically regulated by NADPH and possesses an unusually low $K_m$ for ammonium that ranges from 0.02 to 3.5 mM, depending on the NADPH concentration (Bascomb and Schmidt, supra). The $K_m$ value for ammonium of the α-homohexamer is the lowest reported ammonium $K_m$ for any plant GDH characterized to date. In contrast, the β-homohexamer (catabolic form) is a non-allosteric enzyme with an ammonium $K_m$ of approximately 75 mM. From these studies involving purified enzymes, it is postulated that the heterohexamers have varying degrees of affinity for ammonium. However, no kinetic analyses have been performed on purified heterohexamers.

Although the α- and β-subunits have distinct in vivo turnover rates (Bascomb et al., supra) and the corresponding homohexamers have remarkably different ammonium $K_m$ values, the α- and β-subunits are derived from precursor proteins of nearly identical size (ca 58,000 Daltons) and were shown to have very similar peptide maps (Prunkard et al., supra; Bascomb and Schmidt, supra). Moreover, polyclonal antibodies prepared against the β-homohexamer are capable of immunoprecipitating all of the NADP-GDH isoenzyes (Yeung, A. T., K. J. Turner, N. F. Bascomb, R. R. Schmidt [1981] *Anal. Biochem.* 10:216–228; Bascomb et al., supra), but do not crossreact with the mitochondrial NAD-GDH. In addition, previous research in this laboratory provided genomic cloning and southern blot evidence that indicated the *C. sorokiniana* genome possesses a single NADP-GDH structural gene (Cock, J. M., K. D. Kim, P. W. Miller, R. G. Hutson, R. R. Schmidt [1991] *Plant Mol. Biol.* 17:17–27).

The *C. sorokiniana* nuclear-encoded chloroplastic NADP-specific glutamate dehydrogenases are the only chloroplastic localized GDH sequences isolated and characterized from plants. Although the Chlorella GDH isoenzmes had been well characterized, it has been discovered in the present invention that the two mature subunits arise via specifc processing of two similar precursor proteins encoded by two mRNAs formed by alternative splicing of a pre-mRNA derived from a single nuclear gene. Furthermore, the identification of the cleavage site and amino-terminal peptide sequence of the mature functional GDH subunits critical to understanding the enzymatic regulation previously demonstrated in vitro had not been accomplished prior to the present invention.

SUMMARY OF THE INVENTION

The present invention provides the isolation and characterization of two full-length cDNAs from mRNAs isolated from the unicellular green algae *Chlorella sorodiniana*. The two cDNAs encode the precursor proteins (56.35 kD; 57.85 kD) that are processed to yield the mature α- and β-subunits (53.5 kD; 52.3 kD, respectively) that compose the active NADP-GDH hexameric isoenzymes. The present invention demonstrates that the single NADP-GDH gene is alternatively spliced to yield two mRNAs that encode two different chloroplast precursor proteins which are processed to the mature α- and β-subunits. Also described are useful fragments or mutants of the nucleotide and amino acid sequences which retain the disclosed activity or utility. For example, certain fragments of the amino acid sequences provided herein can be useful as transit peptides, providing the protein with the capability to enter and remain in certain cell compartments. Fragments of the nucleotide sequences which are described herein can be useful, for example, as primers in amplification procedures or as probes to hybridize to complementary sequences of interest. The nucleotide and amino acid sequences and fragments thereof as described herein can also be useful as molecular weight markers or in identifig and conforming the relatedness of other nucleotide sequences, polypeptides, or isoenzymes which pertain to NADP-GDH.

The present invention provides a method to alter the assimilation of inorganic nitrogen into organic nitrogen metabolism of higher plants by expressing glutamate dehydrogenases from C. sorokiniana and/or GDHs isolated from other organisms. The alteration of nitrogen assimilation can have the effect of increasing nitrogen assimilation which, as is well understood in the art, can affect the composition of the plant through the inverse effect on carbon metabolism, e.g., accumulation of carbohydrates. It further provides DNA constructs for use in these methods. The present invention also provides the identification of the amino-terminal sequences of the α- and β-subunits, thus providing the precise molecular information needed to express the GDH with the unique kinetic properties of the C. sorokiniana chloroplastic α- and β-NADP-GDH homohexamers. The present invention also provides crops having an increased yield, improved ammonia assimilatory properties which increase their tolerance of ammonia toxicity, improved osmotic stress tolerance, and improved composition of the crop.

BRIEF DESCRIPTION OF THE SEQUENCES

SEQ ID NO. 1 is the cDNA for the precursor-protein of the α-subunit of an NADP-specffic glutamate dehydrogenase.

SEQ ID NO. 2 is the deduced amino acid sequence of the polynucleotide of SEQ ID NO. 1.

SEQ ID NO. 3 is the cDNA for the precursor-protein of the β-subunit of an NADP-specific glutamate dehydrogenase.

SEQ ID NO. 4 is the deduced amino acid sequence of the polynucleotide of SEQ ID NO. 3.

SEQ ID NO. 5 is the N-terminal sequence for the NADP-GDH α-subunit.

SEQ ID NO. 6 is the N-terminal sequence for the NADP-GDH β-subunit.

SEQ ID NO. 7 is the cDNA sequence in the clone designated pBGDc53.

SEQ ID NO. 8 is a primer which hybridizes to the conserved region of NADP-GDH mRNAs.

SEQ ID NO. 9 is a poly(dT) polynucleotide used as an adaptor primer according to the subject invention.

SEQ ID NO. 10 is a polynucleotide used as a primer according to the subject invention.

SEQ ID NO. 11 is a polynucleotide used as a primer according to the subject invention.

SEQ ID NO. 12 is a polynucleotide used as an adaptor primer according to the subject invention.

SEQ ID NO. 13 is the polynucleotide insert in the clone designated pRGDc 60.

SEQ ID NO. 14 is the polynucleotide insert in the clone designated pRGDc 61.

SEQ ID NO. 15 is the polynucleotide used as a primer according to the subject invention.

SEQ ID NO. 16 is the polynucleotide insert in a clone designated pGDc 63.

SEQ ID NO. 17 is the polynucleotide insert of a clone designated pGDc 64.

SEQ ID NO. 18 is the polynucleotide resulting from ligation of purified fragments of the inserts in the clones designated pBGDc 53 and pGDc 63, according to the subject invention.

SEQ ID NO. 19 is the polynucleotide resulting from ligation of purified inserts of the clones designated pGDc 64 and pBGDc 53.

SEQ ID NO. 20 is a polynucleotide used as a primer according to the subject invention.

SEQ ID NO. 21 is a polynucleotide used as a primer hybridizing to the 3' terminus of the template DNA according to the subject invention.

SEQ ID NO. 22 is a polynucleotide used as a primer according to the subject invention.

SEQ ID NO. 23 is the polynucleotide sequence (cDNA) of the processed, mature NADP-GDH α-subunit.

SEQ ID NO. 24 is the amino acid sequence of the processed, mature NADP-GDH α-subunit.

SEQ ID NO. 25 is the polynucleotide (cDNA) sequence of the processed, mature NADP-GDH β-subunit.

SEQ ID NO. 26 is the amino acid sequence of the processed, mature NADP-GDH β-subunit.

DETAILED DISCRIPTION OF THE INVENTION

The present invention provides, for example, cDNAs for the precursor-proteins of the α- and β-subunits of the ammonium inducible, chloroplast localized NADP-specific glutamate dehydrogenases from Chlorella sorokiniana as shown in SEQ ID NOS. 1 and 3, respectively. The deduced amino acid sequences for the precursor-proteins of the α- and β-subunits of the ammonium inducible, chloroplast localized NADP-specific glutamate dehydrogenases from Chlorella sorokniana are shown in SEQ ID NOS. 2 and 4, respectively.

E. coli hosts containing cDNA inserts were deposited with the American Type Culture Collection (ATCC), 12301 Parklawn Drive, Rockville, Md. 20852 USA. The cultures were assigned the following accession numbers by the repository:

| Culture | Accession number | Deposit date |
|---|---|---|
| E. coli DH5α α-NADP-GDH SEQ No. 1 (+42 bp) | ATCC | |
| E. coli DH5α β-NADP-GDH SEQ No. 1 (−42 bp) | ATCC | |

The subject cultures have been deposited under conditions that assure that access to the culture(s) will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit(s), and in any case, for a period of at least 30 (thirty) years after the date of deposit or for the enforceable life of any patent which may issue disclosing the cultures. The depositor acknowledges the duty to replace the deposit (s) should the depository be unable to furnish a sample when requested, due to the condition of the deposit(s). All restrictions on the availability to the public of the subject culture deposits will be irrevocably removed upon the granting of a patent disclosing them.

Automated amino acid sequence analysis identifies 20 and 10 amino-terminal amino acid residues of the α- and β-subunits, respectively. Alignment of the α- and β-subunit peptide sequences reveals that the two subunits are identical with the exception of an 11-amino acid extension present in the larger α-subunit. Monoclonal antibodies raised against the α-subunit were shown to recognize the β-subunit providing further evidence that the two subunits are nearly identical. The identification of the unique α- and β-subunit processing sites within the precursor proteins provides the molecular mechanism to explain the different kinetic properties of the α- and β-NADP-GDH homohexameric isoenzymes.

The aforementioned data provide the information necessary to engineer plants with a specific GDH that has favorable kinetic properties to influence both carbon and nitrogen metabolism. Based on the high guanine/cytosine content the cDNAs are highly amenable for heterologous expression in higher plants. The introduction of either or both subunits with their chloroplast targeting sequences or with other organellar targeting sequences in heterologous plant systems can improve nitrogen assimilation and influence the carbon/nitrogen balance.

It has been discovered that chloroplast localization is related to, and can be dependent on, the N-terminus of the α- or β-precursor protein. Cleavage of the N-terminus of the precursors yields the mature protein. Accordingly, the chloroplast transit peptide comprises a peptide which forms or is an active fragment which is part of the N-terminus cleaved from the precursor protein. Peptides having conformation similar to these cleaved peptides can also function as transit peptides. The chloroplast-transit peptide comprises the active fragment of the N-terminal peptide cleaved from the α-precursor (a 40-mer) or the β-precursor (a 37-mer). The polynucleotide sequences encoding the chloroplast-transit peptides can be used by persons of ordinary skill in the art to produce chloroplast-transit peptides employed with the peptides described herein, or others known in the art.

Adding, removing, or replacing the chloroplast transit peptide associated with the GDH enzyme can be employed to localize the protein according to need, by means well known in the art. For example, localization of the enyme in a chloroplast of a cell can be achieved by the insertion of a chloroplast transit peptide onto an amino acid sequence lacking such a transit peptide. Species-specific chloroplast-transit peptides can be added or can replace those present to optimize insertion into the chloroplast of a desired species.

Similarly, removal of a chloroplast-transit peptide or production of a recombinant protein lacking the peptide can be utilized to sequester the protein in a cellular compartment other than the chloroplast.

Transformed plants expressing the α-homohexamer can be more tolerant to ammonia toxicity, assimilate ammonium more efficiently, and respond more rapidly to osmotic stress encountered in transiently saline soils by providing glutamate the precursor to the osmoprotectant proline. Expression of, for example, the β-homohexamer or GDH heterohexamers can be used to alter the rate of nitrogen assimilation, favoring accumulation of carbohydrates in fruits and other storage organs.

Following are examples which illustrate procedures, including the best mode, for practicing the invention. These examples should not be construed as limiting. All percentages are by weight and all solvent mixture proportions are by volume unless otherwise noted.

EXAMPLES

C. sorokiiziana chloroplast glutamate dehydroaenases. The chloroplastic glutamate dehydrogenase α- and β-isoenzymes used in the following experiments are naturally produced by an organism characterized as Chlorella sorokiniana.

For kdnetic characterization in both the aminating and deaminating directions, the α- and β-holoenzymes were purified from cells that were accumulating only one form of homohexameric GDH isoenzyme. Table 1 summarizes the $K_m$ values determined for both the α- and β-homohexameric isoenzyme aminating reaction.

TABLE 1

| GDH Isoform | Substrate | $K_m$ Value (mM) |
| --- | --- | --- |
| α-homohexamer | NADPH | 0.14 |
| | $NH_4^+$ | 0.02–3.5 |
| | α-ketoglutarate | 0.35* |
| β-homohexamer | NADPH | 0.14 |
| | $NH_4^+$ | 77 |
| | α-ketoglutarate | 12 |

*after Shatilov, V. R., W. L. Kretovich (1977) Mol. Cell Biochem. 15:201–212.

Table 2 summarizes the $K_m$ values determine for both the α- and β-homohexameric isoenzyme deaminating reaction.

TABLE 2

| GDH Isoform | Substrate | $K_m$ Value (mM) |
| --- | --- | --- |
| α-homohexamer | $NADP^+$ | 0.04 |
| | Glutamate | 38.2 |
| β-homohexamer | NADP+ | 0.04 |
| | Glutamate | 32.3 |

C. sorokiniana culture conditions. The C. sorokiniana cells (UTEX-1230, University of Texas algal culture collection; 3B2NA, Robert R. Schmidt, University of Florida, Microbiology Cell Science Department) were cultured autotrophically as previously descrnied by Prunkard et al., supra in a modified basal salts medium. The modified medium contained in mM concentration: $CaCl_2$, 0.34; $K_2SO_4$, 6.0; $KH_2PO_4$, 18.4; $MgCl_2$, 1.5; in μM concentration $CoCl_2$, 0.189; $CuCl_2$, 0.352; EDTA, 72; $FeCl_3$, 71.6; $H_3BO_3$, 38.8; $MnCl_2$, 10.1; $NH_4VO_4$, 0.20; $(NH_4)_6MO_7O_{24}$, 4.19; $NiCl_2$, 0.19; $SnCl_2$, 0.19; $ZnCl_2$, 0.734. The medium was supplemented with 1 mM $NH_4Cl$, 29 mM $NH_4Cl$, or 29 mM $KNO_3$ as a nitrogen source depending on the experimental conditions. The medium containing $NH_4Cl$ was adjusted to pH 7.4, and medium containing $KNO_3$ was adjusted to pH 6.8 with KOH after autoclaving. Cells were supplied with a 2% (v/v) $CO_2$-air mixture and light intensity sufficient to allow cell division into four progeny.

Purification of the NADP-GDH isoenzymes. For purification of the glutamate dehydrogenase α-isoenzyme, *C. sorokiniana* cells were cultured with continuous light in 29 mM ammonium medium in a 30 L Plexiglas chamber as previously described (Baker, A. L., R. R. Schmidt [1963] *Biochim. Biophys. Acta* 74:75–83). Cells were harvested at 4.0 $OD_{640}$ by centrifugation at 30,000 rpm through a Sharples centrifuge and washed two times in 10 mM Tris (pH 8.5 at 4° C.). Pelleted cells (130 g) were stored at –20° C. in 250 mL centrifuge bottles until use. Purification of NADP-GDH was accomplished using a modified procedure of Yeung et al., supra. Procedural modifications involved the substitution of Sephadex G-200 gel (Pharmacia) for G-150 gel in the gel-filtration coluimn, and the addition of $NADP^+$ as a stabilizer to a final concentration of 0.1 mM to the gel-filtration buffer and all subsequent storage buffers. As a final modification, the $NADP^+$ affinity resin step was omitted and a preparative nondenaturing-PAGE step was substituted (Miller, P. W., W. D. Dunn, R. R. Schmidt [1994] *BioRad US/EG Bulletin* 1897).

The GDH deaminating enzyme assay solution was composed of 44 mM Tris, 20.4 mM glutamate, and 1.02 mM $NADP^+$, pH 8.8. The aminating assay solution was composed of 50 mM Tris, 25 mM α-ketoglutarate, 0.357 mM NADPH, and 0.356 M $(NH_4)_2SO_4$, pH 7.4. One unit of enzyme activity was the amount of NADP-GDH required to reduce or to oxidize 1.0 µmol of $NADP^+$ or NADPH per minute at 38.5° C.

Sephadex G-200 column fractions possessing NADP-GDH activity were pooled and concentrated via Diaflow filtration. The soluble enzyme (68 mg) was protected from oxidation by the addition of DTT to a final concentration of 10 mM, and dialyzed for 30 minutes against 28.8 mM Tris, 192 mM glycine, 2 mM DTT (pH 8.4). The dialysate was clarified by centrifugation at 20,000 g for 10 minutes at 4° C. and was combined with 3 mL of 40% (w/v) sucrose and 1 mL of 0.02% bromophenol blue.

For preparative nondenaturing PAGE, a 3 cm tall 7% acrylamide (w/v, 28 acrylamide: 0.735 bis-acrylamide, pH 8.8) resolving gel, and a 2 cm tall 2% acrylamide (w/v, 1.6 acrylamide: 0.4 bis-acrylamide, pH 6.6) stacking gel were cast in the 28 mm ID gel tube of the Model 491 Prep Cell. All acrylamide stocks were pretreated with AG501-X8 mixed bed resin to remove any contaminating acrylic acid residue to prevent in vitro N-acylation of proteins during electrophoresis. The protein sample was electrophoresed at 15 mA constant power for 20 minutes and then for 3.5 hours at a constant power of 30 mA. Six miliimter fractions were collected and assayed for NADP-GDH deaminating activity and GDH containing fractions were pooled. The enzyme in the pooled fractions in 10 mM $KPO_4$ (pH 6.2), 0.1 mM $NADP^+$ was concentrated by Diaflow ultrafiltration to 1 mg/mL as determined by the method of Bradford, using BSA as a standard. The concentrated enzyme preparation was stored at –20° C. The purity of the preparation was determined by silver-staining to visualize proteins resolved by 10% (w/v) Tris-Tricine SDS-PAGE (Schagger, H., G. von Jagow [1987] *Anal. Biochem.* 166:368–379).

The NADP-GDH β-isoenzyme was purified from a mixture of cells cultured for 240 minutes in 1 mM ammonium medium (14 g), 90 minutes in 1 mM ammonium medium (6 g), and for 20, 40, 60, and 80 minutes in 29 mM ammonium medium (1 g/time point) according to Bascomb and Schmidt, supra. The NADP-GDH β-isoenzyme was partially purified using a scaled down modified procedure of Yeung et al., supra. The DEAE sephacel ion exchange columns (pH 7.4, and pH 6) were scaled down to a 40 mL bed volume and a 400 mL linear KCl gradient (0 to 0.4 M) was used to elute the proteins in 3 mL fractions. The pH 6 DEAE ion-exchange column fractions containing NADP-GDH were combined into two pools; corresponding to the leading and trailing halves of the NADP-GDH activity peak. The separate pooled fractions were dialyzed against 10 mM $KPO_4$ (pH 6.2), 2 mM DTT for 16 hours, and affinity purified using Type 3 $NADP^+$ affnity gel (Pharmacia) as previously described (Bascomb and Schmidt, supra). The NADP-GDH in the pooled fractions was concentrated via Diaflow ultrafiltration to 2 mg/ml protein, as determined by the method of Bradford (Bradford, M. M. [1976] *Anal. Biochem.* 72:248–254), and stored at 4° C. until further use. After resolution of the proteins by 8% (w/v) Tris-Tricine SDS-PAGE, the purity of the preparation was determined by silver staining.

Amino-terminal sequencing of the mature subunits. An aliquot of a preparation of purified NADP-GDH α-subunit (120 pmol) and a partially purified preparation of NADP-GDH α-subunit (80 pmol) and β-subunit (50 pmol) were resolved by 8% (w/v) Tris-Tricine SDS-PAGE and electroblotted to a PVDF membrane (lmmobilon-$P^{SQ}$, Millipore) as described by Plough et al. (Plough, M., A. L. Jensen, V. Barkholt [1989] *Anal. Biochem.* 181:33–39). To prevent in vitro acylation of the protein amino-terminal residues, all polyacrylanide solutions used in PAGE were treated with AG501-X8 mixed bed resin to remove contaminating acrylic acid. An Applied Biosystems, Inc. model 470A gas phase sequencer was utilized for automated Edman degradation amino sequence analysis. The PTH-aa derivatives were identified by RP-HPLC. Protein sequence analysis of the electroblotted proteins was provided by the Interdisciplinary Center for Biotechnology Research Protein Chemistry Core facility at the University of Florida.

The following N-terminal sequence was determined for the α-subunit: AVSLEEQISAMDATTGDFTA (SEQ ID NO. 5). The following N-terminal sequence was determined for the β-subunit: DATTGDFIAL (SEQ ID NO. 6). These sequences are identical to the ORF identified in the two NADP-GDH cDNAs and indicate the positions of the internal cleavage sites utilized to remove the chioroplast targeting peptide sequences. The chloroplast targeting peptide sequences (or chloroplast-transit peptides) can be useful for cell compartment localization with these and other amino acid sequences. The polynucleotides encoding the chloroplast-transit peptides can be used with other polynucleotide sequences to encode chloroplast-transit peptides.

cDNA isolation and sequencing. A pellet of *C. sorokiniana* cells stored at –70° C. was resuspended 1 to 10 (w/v) in RNA breakage buffer: 0.1M Tris (pH 8.5), 0.4M LiCl, 10 mM EGTA, 5 mM EDTA, 100 units/mL sodium heparin (Sigma, 100 units/mg), and 1 mM aurintricarboxylic acid (Sigma). The cell suspension was centrifuged at 7000 g for 5 mrinutes at 4° C. and the supernatant was discarded. The cell pellet was resuspended 1 to 10 (w/v) in RNA breakage buffer and ruptured by passage through a French pressure cell at 20,000 p.s.i. The cell homogenate was collected in a disposable 50 mL conical tube containing 0.05 times volume 20% (w/v) SDS, 0.05 times volume 0.5 M EDTA (pH 8), 200 µg/mL proteinase K, and allowed to incubate at room temperature for 15 minutes. One-half volume of TE buffer (Tris 10 mM:EDTA 1 mM, pH 8.0) equilibrated phenol was added to the homogenate and after a 3 minutes incubation a one-half volume of chloroform:isoamylalcohol (24:1, v/v) was added and mixed for 10 minutes on a wrist action shaker. The extracted homogenate was transferred to a 30 mL siliconized corex tube and centrifuged at 1000 g for 10 minutes at 4° C. The upper aqueous phase was removed and repeatedly extracted with an equal volume of chloroform:isoanmyl-alcohol (24:1, v/v), as descnrbed above, until the aqueous interface was clear. After the final extraction, the aqueous phase was combined with an equal volume of 2× LiCl-Urea buffer (4 M LiCl. 4 M urea, 2 mM EDTA, 1 mM aurintricarboxylic acid; Sigma) and the RNA was precipitated on ice for 16 hours at 4° C. The RNA precipitate was centrifuged at 4000 g for 20 minutes at 4° C. and the resulting pellet was rinsed once with 1× LiCl-Urea buffer and centrifuged again to pellet the RNA. The RNA pellet was solubilized in TE (pH 7.5) and an aliquot was quantified spectrophotometrically at 260 nm. After quantitation, the mRNA fraction was isolated from total cellular RNA using an oligo(dT) spin column kit. Poly(A)$^+$ RNA (50 µg) from each preparation was combined and utilized for the commercial production of a custom λUni-ZAP XR *C. sorokiniana* cDNA library (Stratagene Cloning Systems, Palo Alto, Calif.).

The amplified λZAP library, containing 2×10$^{10}$ pfu/mL, was plated on twenty 150 mm petri plates at 50,000 pfu per plate for a total of 1×10$^6$ pfu screened. The phage plaques were absorbed to duplicate Hybond-N 132 mm circular membranes and treated according to the plaque blotting protocol of Amersham (1985, Amersham International plc, Arlington Heights, Ill.). Membranes were prehybridized in a common container in 200 mL of 2× PIPES (0.8 M NaCl, 20 mM PIPES, pH 6.5), 50% (w/v) formamide, 0.5% (w/v) SDS, 100, µg/mL denatured sheared salmon sperm DNA at 40° C. Blocked membranes were hybridized at 42° C. in ten heat-sealable bags (four membranes/bag) in prehybridization buffer containing 1×10$^6$ cpm/membrane of a $^{32}$P-labeled NADP-GDH 242 bp HCR cDNA probe on a lab rocker. The membranes were washed three times in 200 mL of 0.1× SSC, 0.1% (whv) SDS for 20 minutes per wash at 50° C. Duplicate membranes were wrapped in plastic wrap and exposed to Kodak X-Omat AR film at −70° C. for 28 hours. Putative NADP-GDH cDNA plaques, detected on duplicate membranes, were cored from the plate and plaque purified by secondary and tertiary screenings with the 242 bp conserved region probe. Putative NADP-GDH cDNA phage clones, selected in the primary screening, were combined and screened a second time with a $^{32}$P-labeled 130 bp Eco RI/Bgl II cDNA fragment isolated from the 5' terminus of the most complete 5' end NADP-GDH cDNA clone. Ten plaque pure NADP-GDH clones were subcloned in pBluescript KS$^+$ (Stratagene) and transformed into *E. coli* DH5α F' (Bethesda Research Laboratories, BRL) via an in vivo excision protocol provided by Stratagene. All plasmid isolations were performed as described by Kraft et al. (Kraft, R., J. Tardiff, K. S. Krauter, L. A. Leinwand [1988] *Biotechniques* 6:544–547). Sequence analysis revealed all ten clones were identical at their 3'-termini and differed by varying degrees of truncation at their 5'-termini. The longest cDNA clone with a complete 3'-terminus designated pBGDc53 (SEQ ID NO. 7) was not long enough to encode either subunit; therefore, the 5'-terminal sequences were determined by RACE PCR.

The 5'-terminal NADP-GDH cDNA sequences were cloned using a modified anchored PCR procedure for the rapid amplification of cDNA ends (Frohman, M. A. [1990] In D. H. Gelford, J. J. Snincky, T. J. White, eds, *PCR Protocols*, Academic Press, San Diego, Calif., pp 28–38; Jain, R., R. H. Gomer, J. J. Murtagh [1992] *Biotechniques* 12:5859). A mixture of poly(A)$^+$ RNA, used in the synthesis of the λZAP library, was utilized to clone the 5' end of the NADP-GDH mRNA. One hundred nanograms of the MRNA mixture were combined with 10 ng of a gene-specific primer (5'-CTCAAAGGCAAGGAACTTCATG-3', SEQ ID NO. 8), designed to hybridize to the conserved region of NADP-GDH mRNAs, heated for 5 minutes, and chilled on ice. First strand DNA synthesis was performed using Superscript™ reverse transcriptase (BRL) according to the supplier's protocol. The terminated reverse transcription reaction was treated with one unit of ribonuclease H for 20 minutes at 37° C., 5 minutes at 95° C., and extracted once with chloroform:isoamyl alcohol (24:1, v/v). Excess primers and dNTPs were removed by centrifugation at 2000 rpm through an Ultrafree-MC filterfuge tube (30,000 MW cutoff, Millipore) and the retentate was concentrated to 10 µl on a Savant Speedvac. The first-strand synthesis products were combined with 10 µL of tailing mix (1× tailing buffer [Promega Corp.], 0.4 mM dATP, 10 units terminal deoxytransferase) and incubated at 37° C. for 10 minutes. The reaction mixture was heated to 95° C. for 5 minutes, diluted to 0.5 mL with TE (pH 8), and utilized as a cDNA pool. A mixture of 5 µL of the cDNA pool, 5 µL of Vent™ polymerase 10×buffer (New England Biolabs), 200 µM of each dNTP, 25 pmol of a gene specific primer (SEQ ID NO. 8), 5 pmol of the poly(dT) adaptor primer (5'-GGGTCGACATTCTAGACAGAATTCGTGGATCC(T)$_{18}$-3'; SEQ ID NO. 9), 0.2 units Perfectmatch™ DNA polymerase enhancer (Stratagene), and 1 unit of Vent™ polymerase (NEB) in 50 µL was amplified according to Jain et al., supra. The PCR products were purified away from the excess primers by centrifugation at 2,000 rpm through an Ultrafree-MC unit. The retentate was collected and subjected to two more rounds of amplification using a new nested gene specific primer at each step (5'-GGACGAGTACTGCACGC-3', SEQ ID NO. 10; 5'-GATCTCGGTCAGCAGCTG-3', SEQ ID NO. 11, respectively) and an adaptor primer (5'-GGGTCGACATTCTAGACAGAA-3'; SEQ ID NO. 12). PCR amplifications were performed in a Model 480 thermocycler (Perlin-Elmer Cetus), and all custom oligonucleotides were synthesized by the ICBR DNA synthesis facility, University of Florida. The standard PCR reaction mixture consisted of 10 µL of 10× Vent™ polymerase buffer, 100 µM of each dNTP, 0.4 units of Perfectmatch™, 50 pmol of each primer, 1 unit Vent™ DNA polymerase in a 100 µl reaction volume. The 5' RACE-PCR products were gel purified, subcloned into the SmaI site of pUC 18, and transformed into *E. coli* DH5α for further characterization. RACE PCR identified two 5' cDNA clones, which overlapped with the previously identified pBGDc 53 clone, that differed by a 42 nt insert identified in one clone designated pRGDc 60 (SEQ ID NO. 13) and lacking in the second cDNA designated pRGDc 61 (SEQ ID NO. 14).

Two additional cDNA clones lacking the RACE PCR polylinker, but possessing the complete 5'-termini corresponding to pRGDc 60 and 61 were constructed by RT-PCR amplification from mRNA using reaction conditions as described above and the gene specific primer pair (5'-CTTTCTGCTCGCCCTCTC-3', SEQ ID NO. 15, and SEQ ID NO. 11, above). The two PCR products were cloned into the SmaI site of pBluescript SK+ (Stratagene) and transformed into *E. coli* DH5α for further characterization. The cDNA clone that possessed the 42 nt insert was designated pGDc 63 (SEQ ID NO. 16) whereas the cDNA lacking the insert was designated pGDc 64 (SEQ ID NO. 17).

Full-length NADP-GDH cDNAs were constructed by restriction endonuclease treating pGDc 63 and 64 with EcoRI/ApaLI and gel purifyig the resultant (264 bp; 222 bp, respectively) fragments. The gel purified fragments were ligated to a purified ApaLI/XhoI restriction fragment of pBGDc 53 and the full length ligation products (SEQ ID NO. 18; SEQ ID NO. 19) were gel agarose gel purified and utilized in subsequent PCR reactions.

Expression of α- and β-homohexamers in E. coli. Using the gel purified product (SEQ ID NO. 18), PCR mutagenesis was performed to remove the chloroplast targeting signal from the full-length cDNA and yield cDNAs encoding specifically the mature α- and β-subunits. Two sets of primer pairs were designed to synthesize α- and β-GDH subunit genes.

The following primer was designed to add a methionine to the amino terminus of the processed mature α-NADP-GDH subunit (alanine-41) to allow translation initiation and to generate a 5' NdeI site for subcdoning purposes: 5'-CATATGGCCGTCTCGCTGGAGGAG-3' (SEQ ID NO. 20). The following second primer was designed to hybridize to the 3' terminus of the template DNA at a position 20 nt 3' of the endogenous TAA termination codon: 5'-GTTGGATTGCCGGTGAGCC-3' (SEQ ID NO. 21).

The following primer was designed to add a methionine to the amino terminus of the processed mature β-subunit (aspartate-38) to allow translation initiation and to generate a 5' NdeI site for subcloning purposes: 5'-CATATGGACGCCACCACCGGC-3' (SEQ ID NO.22). The second 3' primer used in the PCR amplification was the 3'-terminus primer (SEQ ID NO. 21) described for the α-subunit amplification.

PCR cycling conditions were as follows: 95° C., 50 seconds; 64° C., 1 minute; 72° C., 1 minute 35 seconds (30 cycles). Primer, DNTP, Vent polymerase, and other reaction component concentrations were as previously described. The 1506 bp α-NADP-GDH subunit gene (SEQ ID NO. 23) and 1473 bp β-GDH subunit gene (SEQ ID NO. 25) PCR products were gel purified and given a 3' adenine nucleotide overhang by incubating the purified fragment with 100 μM dATP and Taq polymerase for 15 minutes at 72° C. The modified PCR products were cloned into the PCRII T/A cloning vector (Invitrogen) and transformed into competent E. coli cells. Clones bearing the inserts were selected by blue-white screening, plasmid purified, and digested with NdeI/BamHI to select for the proper orientation in the cloning vector. The selected plasmids were restricted with NdeI and BamHI (BamHI site provided by vector) and directionally cloned under the control of the IPTG inducible T7 polymerase promoter of pET 11a and pET 15b bacterial expression vectors (Novagen) linearized with NdeI/BamHI, and transformed into DH5α. Transformants were screened by NdeI/BamHI restriction analysis and clones possessing the properly oriented α- and β-subunit cDNAs (SEQ ID NO. 23; SEQ ID NO. 25) were selected, plasmid purified, and transformed into E. coli BL21(DE3) for protein expression purposes.

E. coli BL21(DE3) cells transformed with pET 11a-α-cDNA and pET 11a-β-cDNA constructs were induced with 100 mM IPTG for 1 hour. Protein extracts from the induced cells were tested by enzyme analysis for NADP-GDH activity, and the denatured proteins were resolved by SDS gel electrophoresis, and visualized by coomassie staining.

The proteins expressed by the mature α-subunit cDNA (SEQ ID NO. 23) and the β-subunit cDNA (SEQ ID NO. 25) have the amino acid sequences shown in SEQ ID NO. 24 (α-subunit) and SEQ ID NO. 26 β-subunit). The recombinant GDH subunits were verified by crossreactivity with rabbit anti-Chlorella NADP-GDH antibodies.

Under conditions not optimized for maximal induction, the E. coli cells, possessing the α- and β-GDH cDNAs and induced with IPTG, showed 60- and 7,000-fold increases in NADP-GDH activity relative to uninduced controls, respectively. The recombinant α- and β-NADP-GDHs are currently being analyzed to verify kinetic and biochemical properties.

The over-expression and assembly of the C. sorokiniana chloroplastic GDHs into active enzymes provides proof that the DNA constructs engineered via PCR are transcribed and translated into authentic proteins. The aforementioned constructs were then utilized for cytosolic expression of the algal GDHs in transgenic plants.

Transformation of plants. A method for producing genetically transformed plants that express increased levels of a specific GDH requires the introduction of a double-stranded recombinant DNA molecule into the nuclear genome of a plant cell. The DNA molecule must (1) contain a structural DNA for the GDH enzyme being introduced into the plant cell; (2) possess a promoter which functions in plants to regulate the production of an RNA sequence in a constitutive or tissue-specific manner by RNA polymerase enzyme; and (3) have a 3'-untranslated region which functions to cause transcriptional termination and the addition of polyadenylated nucleotides to the 3' end of the RNA. The resulting primary RNA molecule is subsequently processed in the nucleus, a process which involves the removal of intronic sequences and the addition of polyadenylate nucleotides to the 3' end of the mRNA.

Promoters which are useful in the present invention are those that can initiate transcription in a constitutive manner or in a tissue-specific manner where glutamate production or catabolism is desired. An example of a useful constitutive promoter is the CaMV enhanced 35S promoter that directs the synthesis of RNA in a tissue independent manner. Promoters which cause production of GDH specifically in seeds, stems, roots, leaves, or specific cell types in these tissues are useful in the present invention. For example, the seed-specific Phaseolm promoter is one such tissue-specific promoter. Thus native promoters for maize, wheat, barley, and rice may be obtained and used in the present invention as well as heterologous promoters from other organisms shown to function in a constitutive/tissue-specific manner.

Introns. Generally, optimal expression in monocotyledonous plants is obtained when an intron sequence is inserted between the promoter sequence and the structural gene sequence. An example of such an intron sequence is the HSP 70 intron described in WO 93/19189.

Polyadenylation signal. The DNA constructs of the present invention can possess a 3' untranslated region which functions in plants to direct the addition of polyadenylate nucleotides to the 3' end of the RNA. An example of a suitable 3' untranslated region is the polyadenylation signal of the Agrobactenum tumor inducing plasmid, i.e., nopaline synthatase (NOS) gene.

Plastid targeting sequence. The DNA constructs of the present invention can optionally contain a plastid targeting sequence. The plastid targeting sequence directs the import of the protein into the plastid, and is removed during importation. The plastid targeting sequence can be, but is not limited to, the native chloroplast targeting peptide (CTP) identified in the *C. sorokiniana* NADP-GDH full-length cDNAs which encode the precursor proteins. A fusion of a selected plastid targeting sequence and the mature α- and β-NADP-GDH subunit sequences can be made by standard procedures and used in the present invention. GDH subunits lacking these targeting sequences are typically found in the cytoplasm of the cell. Such a cytosolic localized enzyme can be useful in capturing ammonium or glutamate compartmentalized in the cytosol of the cell.

GDH gene sources. The GDH gene used in the DNA constructs of the present invention can be any GDH gene. It is not limited to the *C. sorokiniana* GDH genes described above, although they are preferred. For example, a GDH gene from bacteria or fungi can be used. The examples provided use the α- and β-GDH genes of *C. sorokiniana*, but should not be interpreted in any way to limit the scope of the present invention. Individuals skilled in the art will recognize that various other genes as well as alterations can be made to genes and methods described herein while not departing from the spirit and scope of the present invention. For example, mutagenesis and routine screening can be implemented by techniques well known in the art to produce mutant variants that lack regulation by the cofactor NADPH.

Transient expression in maize protoplasts. In order to test the expression of the *C. sorokiniana* GDH subunits and their assembly into active enzymes in *Zea mays* cells, vectors were constructed to contain the CaMV E35S promoter, the coding sequence for the mature α-subunit (pMON21904) or β-subunit (pMON21905), the NOS 3'-untranslated polyadenylation region, and kanamycin resistance for selection in *E. coli*. The α- and β-subunit genes were isolated as a XbaI-EcoRI fragment from pET 11a-α-cDNA and pET 11a-β-cDNA, respectively. The GDH genes were ligated into the XbaI-EcoRI E35S promoter, NOS 3', kanamycin resistance bearing region of pMON22072 to give pMON21904, and pMON21905. The DNA constructs were electroporated into maize and wheat protoplast according to the method of Sheen et al. (*The Plant Cell* Vol. 3, 225–245).

Analysis of transformed maize protoplasts. Pelleted protoplast samples transformed with pMON21904 (α-subunit), pMON21905 (β-subunit), pMON21709 (kanamycin negative control DNA), and no DNA were thawed in 0.2 mL of GDH cell breakage buffer (Yeung et al., supra) on ice. The cells in each suspension were homogenized twice for 30 seconds, chilled on ice, and clarified at 14,000 rpm for 10 minutes. Cell extracts were assayed in the deaminating direction at 38.5° C. according to Yeung et al., supra. Total protein content of the cell extracts was determined using the BioRad microprotein assay according to the manufacturer's protocol. Activities were normalized against total protein content for comparisons among different preparations. One unit of GDH activity is defined as the amount of enzyme necessary to reduce 1 μmol of NADP per minute at 38.5° C.

Protoplasts transformed with the control vector pMON21709 (n=3) or protoplasts not transformed (n=3) had no detectable NADP-GDH activity. Protoplasts transformed with pMON21904 (n=3) expressed 3.31 Units $mg^{-1}$ protein of GDH actvity, whereas pMON21905 transformed protoplasts (n=3) 1.96 Units $mg^{-1}$ protein.

The high level of activity observed for the protoplasts transformed with the cytoplasmic expressed *C. sorokiniana* α- and β-NADP-GDH genes provides evidence that the GDH subunits are expressed in heterologous plant systems. Additionally, expression levels demonstrate that the subunits are assembled into active enzymes. Generally, it would be readily apparent to persons of ordinary skill in the art that superfluous sequences added to the described sequences, or fragments of the nucleotide or amino acid sequences descibed herein, which result in polynucleotides or amino acid sequences that function similarly or equivalently to the sequences expressly descnrbed herein, should also be considered part of this invention. They can easily and routinely be produced by techniques well known in the art, for example, by time-controlled Bal31 exonuclease digestion of the full-length DNA, followed by expression of the resulting fragments and routine screening of the expression products as described in the foregoing example. In addition, it would be readily accepted by ordinarily skilled artisans that the function, property, or utility of the described sequences can be negatived by inserting mutations into the sequences by standard techniques and procedures. These mutations which, by implication, effectively serve to remove the property or function inherent in the sequences as described are hereby expressly included as part of the invention. For example, a clear distinction between the α- and β-subunits of the *C. sorokiniana* is the 11-amino acid polypeptide sequence at the N-terminus of the α-subunit, but absent in the β-subunit. This sequence can affect the affinity, specificity, and modulation of ammonium compounds by the enzyme. Therefore, it would be apparent that inserting (if absent) or removing (if present) the appropriate sequence, or its functional equivalent, to effect a difference in certain characteristics of other GDH genes, or their products, would be easily carried out by those persons.

It should also be understood that the examples and embodiments described herein are for illustrative purposes only and that various modifications or changes in light thereof will be suggested to persons skilled in the art and are to be included within the scope and purview of this application and the scope of the appended claims.

We claim:

1. An isolated polypeptide comprising an amino acid sequence selectedfrom the group consisting of SEQ ID NO: 2, SEQ ID NO: 4, SEQ ID NO: 24, SEQ ID NO: 26, and fragments of any of the foregoing that exhibit α-GDH enzymatic activity, β-GDH enzymatic activity, or chloroplast-transit peptide activity.

2. A polypeptide according to claim 1, said polypeptide comprising an amino acid sequence selected from the group consisting of SEQ. ID NO: 2 and fragments thereof sufficient to exhibit α-GDH enzymatic activity or chloroplast-transit peptide activity.

3. A polypeptide according to claim 1, said polypeptide comprising an amino acid sequence selected from the group consisting of SEQ. ID NO: 4 and fragments thereof sufficient to exhibit β-GDH enzymatic activity or chloroplast-transit peptide activity.

4. A polypeptide according to claim 1, said polypeptide comprising an amino acid sequence selected from the group consisting of SEQ. ID NO: 24 and fragments thereof sufficient to exhibit α-GDH enzymatic activity.

5. A polypeptide according to claim 1, said polypeptide comprising an amino acid sequence selected from the group consisting of SEQ. ID NO: 26 and fragments thereof sufficient to exhibit β-GDH enzymatic activity.

6. A polypeptide according to claim 2, said polypeptide comprising the amino acid sequence of SEQ. ID NO: 2.

7. A polypeptide according to claim 3, said polypeptide comprising the amino acid sequence of SEQ. ID NO: 4.

8. A polypeptide according to claim 4, said polypeptide comprising the amino acid sequence of SEQ. ID NO: 24.

9. A polypeptide according to claim 5, said polypeptide comprising the amino acid sequence of SEQ. ID NO: 26.

10. An isolated chloroplast-transit peptide comprising an amino acid sequence elected from the group consisting of residues 1 through 40 of SEQ ID NO: 2, residues 1 through 26 of SEQ ID NO: 4, and fragments of any of the foregoing sufficient to exhibit chloroplast-transit peptide activity.

11. A chloroplast-transit peptide according to claim 10, said peptide having the amino acid sequence of residues 1–40 of SEQ ID NO: 2.

12. A chloroplast-transit peptide according to claim 10, said choroplast-transit peptide having the amino acid sequence of residues 1–26 of SEQ ID NO: 4.

13. A chloroplast-transit peptide according to claim 10 wherein said chloroplast-transit peptide is attached to a heterologous amino acid sequence.

14. A chloroplast-transit peptide according to claim 11 wherein said chloroplast-transit peptide is attached to a heterologous amino acid sequence.

15. A chloroplast-transit peptide according to claim 12 wherein said chloroplast-transit peptide is attached to a heterologous amino acid sequence.

* * * * *

UNITED STATES PATENT AND TRADEMARK OFFICE
CERTIFICATE OF CORRECTION

PATENT NO. : 5,985,634
DATED : November 16, 1999
INVENTOR(S) : Robert R. Schmidt and Philip Miller It is certified that error appears in the above-indentified patent and that said Letters Patent is hereby corrected as shown below:

Abstract, line 3, "descnred" should read --described--.

Abstract, line 4, "sorokinina" should read --sorokiniana--.

Column 1, line 18, "almnation" should read --amination--

Column 1, line 53 "N.E." should read --N.F.--

Column 1, line 60, "Chlorefla" should read --Chlorella--

Column 2, line 4, "lift" should read --light--.

Column 2, line 32, "isoenzyes" should read --isoenzymes--.

Column 2, line 44, "isoenzmes" should ready --isoenzymes--.

Column 2, line 47, "specifc" should read --specific--.

Column 2, line 60, "sorodiniana" should read --sorokiniana--.

UNITED STATES PATENT AND TRADEMARK OFFICE
CERTIFICATE OF CORRECTION

PATENT NO. : 5,985,634
DATED : November 16, 1999
INVENTOR(S) : Robert R. Schmidt and Philip Miller It is certified that error appears in the above-indentified patent and that said Letters Patent is hereby corrected as shown below:

Column 3, line 13, "identifig" should read --identifying--.

Column 4, line 44 "sorokniana" should read --sorokiniana--.

Column 4, line 51 should read:

| Culture | Accession number | Deposit date |
|---|---|---|
| *E. coli* DH5α α-NADP-GDH SEQ No. 1 (+42 bp) | ATCC 69925 | October 6, 1995 |
| *E. coli* DH5α β-NADP-GDH SEQ No. 3 (-42 bp) | ATCC 69926 | October 6, 1995 |

Column 5, line 10 "furrishing" should read --furnishing--.

UNITED STATES PATENT AND TRADEMARK OFFICE
CERTIFICATE OF CORRECTION

PATENT NO. : 5,985,634
DATED : November 16, 1999
INVENTOR(S) : Robert R. Schmidt and Philip It is certified that error appears in the above-indentified patent and that said Letters Patent is hereby corrected as shown below:

Column 6, line 21, "sorokiiziana" should read --sorokiniana--.

Column 6, line 26, "kdnetic" should ready --kinetic--.

Column 6, line 60, "descrnied" should read --described--.

Column 7, line 55, "miliimter" should read --milliliter--.

Column 8, line 29, "(lmmobilon" should read --(Immobilon--.

Column 8, line 45, "DATTGDFIAL" should read --DATTGDFTAL--

Column 8, line 61, "mrinutes" should read --minutes--.

Column 9, line 10, "isoanmyl-alcohol" should read --isomylalcohol--.

Column 9, line 41, "(why)" should read --(w/v)--

UNITED STATES PATENT AND TRADEMARK OFFICE
CERTIFICATE OF CORRECTION

PATENT NO. : 5,985,634
DATED : November 16, 1999
INVENTOR(S) : Robert R. Schmidt and Philip Miller It is certified that error appears in the above-indentified patent and that said Letters Patent is hereby corrected as shown below:

Column 10, line 4, "Gomer" should read --Gorner--.

Column 10, line 45, "(Perlin" should read --Perkin--.

Column 11, line 22, "subsdoning" should read --subcloning--

Column 12, line 45, "Phaseolm" should read --Phaseolin--.

Column 12, line 61, "Agrobactenum" should read --Agrobacterium--.

Column 14, line 22, "descnrbed" should read --described--.

Column 14, line 50, "scope" should read --spirit--.

Column.54, line 39 (claim 33, line 1), "elected" should read --selected--

Signed and Sealed this

Twentieth Day of March, 2001

*Attest:*

NICHOLAS P. GODICI

*Attesting Officer*   Acting Director of the United States Patent and Trademark Office

UNITED STATES PATENT AND TRADEMARK OFFICE
CERTIFICATE OF CORRECTION

PATENT NO. : 5,985,634
DATED : November 16, 1999
INVENTOR(S) : Robert R. Schmidt and Philip Miller It is certified that error appears in the above-identified patent and that said Letters Patent is hereby corrected as shown below:

Column 1,
Line 5, (after the title of the invention), please insert the following new paragraph:

-- This invention was made with government support under USDA Competitive Grant Number 87-CRCR-1-2476. The government has certain rights in this invention. --

Signed and Sealed this

Sixth Day of November, 2001

Attest:

*Nicholas P. Godici*

NICHOLAS P. GODICI
*Attesting Officer*  *Acting Director of the United States Patent and Trademark Office*

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 2140 base pairs
      (B) TYPE: nucleic acid
      (C) STRANDEDNESS: double
      (D) TOPOLOGY: linear (ii) MOLECULE TYPE: cDNA (ix) FEATURE:
    (A) NAME/KEY: CDS
    (B) LOCATION: 33..1610

(xi) SEQUENCE DESCRIPTION: SEQ ID NO:1:

```
TCCTTTCTG CTCGCCCTCT CTCCGTCCCG CC ATG CAG ACC GCC CTC GTC GCC        53
                                  Met Gln Thr Ala Leu Val Ala
                                   1               5

AAG CCT ATC GTG GCC GCC CCG CTG GCG GCA CGC CCG CGC TGC CTC GCG      101
Lys Pro Ile Val Ala Ala Pro Leu Ala Ala Arg Pro Arg Cys Leu Ala
            10                  15                  20

CCG TGG CCG TGC GCG TGG GTC CGC TCC GCC AAG CGC GAT GTC CGC GCC      149
Pro Trp Pro Cys Ala Trp Val Arg Ser Ala Lys Arg Asp Val Arg Ala
 25                  30                  35

AAG GCC GTC TCG CTG GAG GAG CAG ATC TCC GCG ATG GAC GCC ACC ACC      197
Lys Ala Val Ser Leu Glu Glu Gln Ile Ser Ala Met Asp Ala Thr Thr
 40                  45                  50                  55

GGC GAC TTC ACG GCG CTG CAG AAG GCG GTG AAG CAG ATG GCC ACC AAG      245
Gly Asp Phe Thr Ala Leu Gln Lys Ala Val Lys Gln Met Ala Thr Lys
                60                  65                  70

GCG GGC ACT GAG GGC CTG GTG CAC GGC ATC AAG AAC CCC GAC GTG CGC      293
Ala Gly Thr Glu Gly Leu Val His Gly Ile Lys Asn Pro Asp Val Arg
     75                  80                  85

CAG CTG CTG ACC GAG ATC TTC ATG AAG GAC CCG GAG CAG CAG GAG TTC      341
Gln Leu Leu Thr Glu Ile Phe Met Lys Asp Pro Glu Gln Gln Glu Phe
         90                  95                 100

ATG CAG GCG GTG CGC GAG GTG GCC GTC TCC CTG CAG CCC GTG TTC GAG      389
Met Gln Ala Val Arg Glu Val Ala Val Ser Leu Gln Pro Val Phe Glu
    105                 110                 115

AAG CGC CCC GAG CTG CTG CCC ATC TTC AAG CAG ATC GTT GAG CCT GAG      437
Lys Arg Pro Glu Leu Leu Pro Ile Phe Lys Gln Ile Val Glu Pro Glu
120                 125                 130                 135

CGC GTG ATC ACC TTC CGC GTG TCC TGG CTG GAC GAC GCC GGC AAC CTG      485
Arg Val Ile Thr Phe Arg Val Ser Trp Leu Asp Asp Ala Gly Asn Leu
                140                 145                 150

CAG GTC AAC CGC GGC TTC CGC GTG CAG TAC TCG TCC GCC ATC GGC CCC      533
Gln Val Asn Arg Gly Phe Arg Val Gln Tyr Ser Ser Ala Ile Gly Pro
            155                 160                 165

TAC AAG GGC GGC CTG CGC TTC CAC CCC TCC GTG AAC CTG TCC ATC ATG      581
Tyr Lys Gly Gly Leu Arg Phe His Pro Ser Val Asn Leu Ser Ile Met
        170                 175                 180

AAG TTC CTT GCC TTT GAG CAG ATC TTC AAG AAC AGC CTG ACC ACC CTG      629
Lys Phe Leu Ala Phe Glu Gln Ile Phe Lys Asn Ser Leu Thr Thr Leu
    185                 190                 195

CCC ATG GGC GGC GGC AAG GGC GGC TCC GAC TTC GAC CCC AAG GGC AAG      677
Pro Met Gly Gly Gly Lys Gly Gly Ser Asp Phe Asp Pro Lys Gly Lys
200                 205                 210                 215

AGC GAC GCG GAG GTG ATG CGC TTC TGC CAG TCC TTC ATG ACC GAG CTG      725
Ser Asp Ala Glu Val Met Arg Phe Cys Gln Ser Phe Met Thr Glu Leu
                220                 225                 230

CAG CGC CAC ATC AGC TAC GTG CAG GAC GTG CCC GCC GGC GAC ATC GGC      773
Gln Arg His Ile Ser Tyr Val Gln Asp Val Pro Ala Gly Asp Ile Gly
            235                 240                 245

GTG GGC GCG CGC GAG ATT GGC TAC CTT TTC GGC CAG TAC AAG CGC ATC      821
Val Gly Ala Arg Glu Ile Gly Tyr Leu Phe Gly Gln Tyr Lys Arg Ile
        250                 255                 260

ACC AAG AAC TAC ACC GGC GTG CTG ACC CCG AAG GGC CAG GAG TAT GGC      869
Thr Lys Asn Tyr Thr Gly Val Leu Thr Pro Lys Gly Gln Glu Tyr Gly
    265                 270                 275
```

```
GGC TCC GAG ATC CGC CCC GAG GCC ACC GGC TAC GGC GCC GTG CTG TTT      917
Gly Ser Glu Ile Arg Pro Glu Ala Thr Gly Tyr Gly Ala Val Leu Phe
280                 285                 290                 295

GTG GAG AAC GTG CTG AAG GAC AAG GGC GAG AGC CTC AAG GGC AAG CGC      965
Val Glu Asn Val Leu Lys Asp Lys Gly Glu Ser Leu Lys Gly Lys Arg
                300                 305                 310

TGC CTG GTG TCT GGC GCG GGC AAC GTG GCC CAG TAC TGC GCG GAG CTG     1013
Cys Leu Val Ser Gly Ala Gly Asn Val Ala Gln Tyr Cys Ala Glu Leu
            315                 320                 325

CTG CTG GAG AAG GGC GCC ATC GTG CTG TCG CTG TCC GAC TCC CAG GGC     1061
Leu Leu Glu Lys Gly Ala Ile Val Leu Ser Leu Ser Asp Ser Gln Gly
        330                 335                 340

TAC GTG TAC GAG CCC AAC GGC TTC ACG CGC GAG CAG CTG CAG GCG GTG     1109
Tyr Val Tyr Glu Pro Asn Gly Phe Thr Arg Glu Gln Leu Gln Ala Val
    345                 350                 355

CAG GAC ATG AAG AAG AAG AAC AAC AGC GCC CGC ATC TCC GAG TAC AAG     1157
Gln Asp Met Lys Lys Lys Asn Asn Ser Ala Arg Ile Ser Glu Tyr Lys
360                 365                 370                 375

AGC GAC ACC GCC GTG TAT GTG GGC GAC CGC CGC AAG CCT TGG GAG CTG     1205
Ser Asp Thr Ala Val Tyr Val Gly Asp Arg Arg Lys Pro Trp Glu Leu
                380                 385                 390

GAC TGC CAG GTG GAC ATC GCC TTC CCC TGC GCC ACC CAG AAC GAG ATC     1253
Asp Cys Gln Val Asp Ile Ala Phe Pro Cys Ala Thr Gln Asn Glu Ile
            395                 400                 405

GAT GAG CAC GAC GCC GAG CTG CTG ATC AAG CAC GGC TGC CAG TAC GTG     1301
Asp Glu His Asp Ala Glu Leu Leu Ile Lys His Gly Cys Gln Tyr Val
        410                 415                 420

GTG GAG GGC GCC AAC ATG CCC TCC ACC AAC GAG GCC ATC CAC AAG TAC     1349
Val Glu Gly Ala Asn Met Pro Ser Thr Asn Glu Ala Ile His Lys Tyr
    425                 430                 435

AAC AAG GCC GGC ATC ATC TAC TGC CCC GGC AAG GCG GCC AAC GCC GGC     1397
Asn Lys Ala Gly Ile Ile Tyr Cys Pro Gly Lys Ala Ala Asn Ala Gly
440                 445                 450                 455

GGC GTG GCG GTC AGC GGC CTG GAG ATG ACC CAG AAC CGC ATG AGC CTG     1445
Gly Val Ala Val Ser Gly Leu Glu Met Thr Gln Asn Arg Met Ser Leu
                460                 465                 470

AAC TGG ACT CGC GAG GAG GTT CGC GAC AAG CTG GAG CGC ATC ATG AAG     1493
Asn Trp Thr Arg Glu Glu Val Arg Asp Lys Leu Glu Arg Ile Met Lys
            475                 480                 485

GAC ATC TAC GAC TCC GCC ATG GGG CCG TCC CGC AGA TAC AAT GTT GAC     1541
Asp Ile Tyr Asp Ser Ala Met Gly Pro Ser Arg Arg Tyr Asn Val Asp
        490                 495                 500

CTG GCT GCG GGC GCC AAC ATC GCG GGC TTC ACC AAG GTG GCT GAT GCC     1589
Leu Ala Ala Gly Ala Asn Ile Ala Gly Phe Thr Lys Val Ala Asp Ala
    505                 510                 515

GTC AAG GCC CAG GGC GCT GTT TAAGCTGCCC AGGCCCAAGC CACGGCTCAC        1640
Val Lys Ala Gln Gly Ala Val
520                 525

CGGCAATCCA ACCCAACCAA CTCAACGGCC AGGACCTTTT CGGAAGCGGC GCCTTTTTCC   1700

CAGCCAGGGC CCTCACCTGC CCTTTCATAA CCCTGCTATT GCCGCCGTGC CCCTGCAATT   1760

CCACCCCAAG AAGAACTAGC GGCACTTGAC TGCATCAGGA CGGCTATTTT TTTCGCGACG   1820

CGCGCTCACC CCGAGAGCCT CTCTCCCCCG AGCCCTAAGC GCTGACGTCC GCCCGACTTT   1880

GCCTCGCACA TCGCTCGGTT TTGACCCCCT CCAGTCTACC CACCCTGTTG TGAAGCCTAC   1940

CAGCTCAATT GCCTTTTAGT GTATGTGCGC CCCCTCCTGC CCCCGAATTT TCCTGCCATG   2000

AGACGTGCGG TTCCTAGCCT GGTGACCCCA AGTAGCAGTT AGTGTGCGTG CCTTGCCCTG   2060

CGCTGCCCGG GATGCGATAC TGTGACCTGA GAGTGCTTGT GTAAACACGA CGAGTCAAAA   2120
```

AAAAAAAAAA AAAAAAAAAA                                              2140

(2) INFORMATION FOR SEQ ID NO:2:

(i) SEQUENCE CHARACTERISTICS:
        (A) LENGTH: 526 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gln Thr Ala Leu Val Ala Lys Pro Ile Val Ala Ala Pro Leu Ala
 1               5                  10                  15

Ala Arg Pro Arg Cys Leu Ala Pro Trp Pro Cys Ala Trp Val Arg Ser
            20                  25                  30

Ala Lys Arg Asp Val Arg Ala Lys Ala Val Ser Leu Glu Glu Gln Ile
        35                  40                  45

Ser Ala Met Asp Ala Thr Thr Gly Asp Phe Thr Ala Leu Gln Lys Ala
    50                  55                  60

Val Lys Gln Met Ala Thr Lys Ala Gly Thr Glu Gly Leu Val His Gly
65                  70                  75                  80

Ile Lys Asn Pro Asp Val Arg Gln Leu Leu Thr Glu Ile Phe Met Lys
                85                  90                  95

Asp Pro Glu Gln Gln Glu Phe Met Gln Ala Val Arg Glu Val Ala Val
            100                 105                 110

Ser Leu Gln Pro Val Phe Glu Lys Arg Pro Glu Leu Leu Pro Ile Phe
        115                 120                 125

Lys Gln Ile Val Glu Pro Glu Arg Val Ile Thr Phe Arg Val Ser Trp
    130                 135                 140

Leu Asp Asp Ala Gly Asn Leu Gln Val Asn Arg Gly Phe Arg Val Gln
145                 150                 155                 160

Tyr Ser Ser Ala Ile Gly Pro Tyr Lys Gly Gly Leu Arg Phe His Pro
                165                 170                 175

Ser Val Asn Leu Ser Ile Met Lys Phe Leu Ala Phe Glu Gln Ile Phe
            180                 185                 190

Lys Asn Ser Leu Thr Thr Leu Pro Met Gly Gly Gly Lys Gly Gly Ser
        195                 200                 205

Asp Phe Asp Pro Lys Gly Lys Ser Asp Ala Glu Val Met Arg Phe Cys
    210                 215                 220

Gln Ser Phe Met Thr Glu Leu Gln Arg His Ile Ser Tyr Val Gln Asp
225                 230                 235                 240

Val Pro Ala Gly Asp Ile Gly Val Gly Ala Arg Glu Ile Gly Tyr Leu
                245                 250                 255

Phe Gly Gln Tyr Lys Arg Ile Thr Lys Asn Tyr Thr Gly Val Leu Thr
            260                 265                 270

Pro Lys Gly Gln Glu Tyr Gly Gly Ser Glu Ile Arg Pro Glu Ala Thr
        275                 280                 285

Gly Tyr Gly Ala Val Leu Phe Val Glu Asn Val Leu Lys Asp Lys Gly
    290                 295                 300

Glu Ser Leu Lys Gly Lys Arg Cys Leu Val Ser Gly Ala Gly Asn Val
305                 310                 315                 320

Ala Gln Tyr Cys Ala Glu Leu Leu Leu Glu Lys Gly Ala Ile Val Leu
                325                 330                 335

Ser Leu Ser Asp Ser Gln Gly Tyr Val Tyr Glu Pro Asn Gly Phe Thr
            340                 345                 350
```

5,985,634

21

22

-continued

```
Arg Glu Gln Leu Gln Ala Val Gln Asp Met Lys Lys Asn Asn Ser
        355                 360                 365

Ala Arg Ile Ser Glu Tyr Lys Ser Asp Thr Ala Val Tyr Val Gly Asp
        370                 375                 380

Arg Arg Lys Pro Trp Glu Leu Asp Cys Gln Val Asp Ile Ala Phe Pro
385                 390                 395                 400

Cys Ala Thr Gln Asn Glu Ile Asp Glu His Asp Ala Glu Leu Leu Ile
                405                 410                 415

Lys His Gly Cys Gln Tyr Val Val Glu Gly Ala Asn Met Pro Ser Thr
            420                 425                 430

Asn Glu Ala Ile His Lys Tyr Asn Lys Ala Gly Ile Ile Tyr Cys Pro
        435                 440                 445

Gly Lys Ala Ala Asn Ala Gly Val Ala Val Ser Gly Leu Glu Met
    450                 455                 460

Thr Gln Asn Arg Met Ser Leu Asn Trp Thr Arg Glu Glu Val Arg Asp
465                 470                 475                 480

Lys Leu Glu Arg Ile Met Lys Asp Ile Tyr Asp Ser Ala Met Gly Pro
                485                 490                 495

Ser Arg Arg Tyr Asn Val Asp Leu Ala Ala Gly Ala Asn Ile Ala Gly
                500                 505                 510

Phe Thr Lys Val Ala Asp Ala Val Lys Ala Gln Gly Ala Val
        515                 520                 525
```

(2) INFORMATION FOR SEQ ID NO:3:

(i) SEQUENCE CHARACTERISTICS:
        (A) LENGTH: 2099 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 33..1568

(xi) SEQUENCE DESCRIPTION: SEQ ID NO:3:

```
CTCCTTTCTG CTCGCCCTCT CTCCGTCCCG CC ATG CAG ACC GCC CTC GTC GCC      53
                                   Met Gln Thr Ala Leu Val Ala
                                    1               5

AAG CCT ATC GTG GCC TGC GCG TGG GTC CGC TCC GCC AAG CGC GAT GTC     101
Lys Pro Ile Val Ala Cys Ala Trp Val Arg Ser Ala Lys Arg Asp Val
        10                  15                  20

CGC GCC AAG GCC GTC TCG CTG GAG GAG CAG ATC TCC GCG ATG GAC GCC     149
Arg Ala Lys Ala Val Ser Leu Glu Glu Gln Ile Ser Ala Met Asp Ala
    25                  30                  35

ACC ACC GGC GAC TTC ACG GCG CTG CAG AAG GCG GTG AAG CAG ATG GCC     197
Thr Thr Gly Asp Phe Thr Ala Leu Gln Lys Ala Val Lys Gln Met Ala
40                  45                  50                  55

ACC AAG GCG GGC ACT GAG GGC CTG GTG CAC GGC ATC AAG AAC CCC GAC     245
Thr Lys Ala Gly Thr Glu Gly Leu Val His Gly Ile Lys Asn Pro Asp
                60                  65                  70

GTG CGC CAG CTG CTG ACC GAG ATC TTC ATG AAG GAC CCG GAG CAG CAG     293
Val Arg Gln Leu Leu Thr Glu Ile Phe Met Lys Asp Pro Glu Gln Gln
            75                  80                  85

GAG TTC ATG CAG GCG GTG CGC GAG GTG GCC GTC TCC CTG CAG CCC GTG     341
Glu Phe Met Gln Ala Val Arg Glu Val Ala Val Ser Leu Gln Pro Val
        90                  95                  100

TTC GAG AAG CGC CCC GAG CTG CTG CCC ATC TTC AAG CAG ATC GTT GAG     389
```

```
                Phe Glu Lys Arg Pro Glu Leu Leu Pro Ile Phe Lys Gln Ile Val Glu
                    105                 110                 115

CCT GAG CGC GTG ATC ACC TTC CGC GTG TCC TGG CTG GAC GAC GCC GGC             437
Pro Glu Arg Val Ile Thr Phe Arg Val Ser Trp Leu Asp Asp Ala Gly
120                 125                 130                 135

AAC CTG CAG GTC AAC CGC GGC TTC CGC GTG CAG TAC TCG TCC GCC ATC             485
Asn Leu Gln Val Asn Arg Gly Phe Arg Val Gln Tyr Ser Ser Ala Ile
                140                 145                 150

GGC CCC TAC AAG GGC GGC CTG CGC TTC CAC CCC TCC GTG AAC CTG TCC             533
Gly Pro Tyr Lys Gly Gly Leu Arg Phe His Pro Ser Val Asn Leu Ser
            155                 160                 165

ATC ATG AAG TTC CTT GCC TTT GAG CAG ATC TTC AAG AAC AGC CTG ACC             581
Ile Met Lys Phe Leu Ala Phe Glu Gln Ile Phe Lys Asn Ser Leu Thr
        170                 175                 180

ACC CTG CCC ATG GGC GGC GGC AAG GGC GGC TCC GAC TTC GAC CCC AAG             629
Thr Leu Pro Met Gly Gly Gly Lys Gly Gly Ser Asp Phe Asp Pro Lys
    185                 190                 195

GGC AAG AGC GAC GCG GAG GTG ATG CGC TTC TGC CAG TCC TTC ATG ACC             677
Gly Lys Ser Asp Ala Glu Val Met Arg Phe Cys Gln Ser Phe Met Thr
200                 205                 210                 215

GAG CTG CAG CGC CAC ATC AGC TAC GTG CAG GAC GTG CCC GCC GGC GAC             725
Glu Leu Gln Arg His Ile Ser Tyr Val Gln Asp Val Pro Ala Gly Asp
                220                 225                 230

ATC GGC GTG GGC GCG CGC GAG ATT GGC TAC CTT TTC GGC CAG TAC AAG             773
Ile Gly Val Gly Ala Arg Glu Ile Gly Tyr Leu Phe Gly Gln Tyr Lys
                235                 240                 245

CGC ATC ACC AAG AAC TAC ACC GGC GTG CTG ACC CCG AAG GGC CAG GAG             821
Arg Ile Thr Lys Asn Tyr Thr Gly Val Leu Thr Pro Lys Gly Gln Glu
        250                 255                 260

TAT GGC GGC TCC GAG ATC CGC CCC GAG GCC ACC GGC TAC GGC GCC GTG             869
Tyr Gly Gly Ser Glu Ile Arg Pro Glu Ala Thr Gly Tyr Gly Ala Val
    265                 270                 275

CTG TTT GTG GAG AAC GTG CTG AAG GAC AAG GGC GAG AGC CTC AAG GGC             917
Leu Phe Val Glu Asn Val Leu Lys Asp Lys Gly Glu Ser Leu Lys Gly
280                 285                 290                 295

AAG CGC TGC CTG GTG TCT GGC GCG GGC AAC GTG GCC CAG TAC TGC GCG             965
Lys Arg Cys Leu Val Ser Gly Ala Gly Asn Val Ala Gln Tyr Cys Ala
                300                 305                 310

GAG CTG CTG CTG GAG AAG GGC GCC ATC GTG CTG TCG CTG TCC GAC TCC            1013
Glu Leu Leu Leu Glu Lys Gly Ala Ile Val Leu Ser Leu Ser Asp Ser
                315                 320                 325

CAG GGC TAC GTG TAC GAG CCC AAC GGC TTC ACG CGC GAG CAG CTG CAG            1061
Gln Gly Tyr Val Tyr Glu Pro Asn Gly Phe Thr Arg Glu Gln Leu Gln
                330                 335                 340

GCG GTG CAG GAC ATG AAG AAG AAG AAC AAC AGC GCC CGC ATC TCC GAG            1109
Ala Val Gln Asp Met Lys Lys Lys Asn Asn Ser Ala Arg Ile Ser Glu
345                 350                 355

TAC AAG AGC GAC ACC GCC GTG TAT GTG GGC GAC CGC CGC AAG CCT TGG            1157
Tyr Lys Ser Asp Thr Ala Val Tyr Val Gly Asp Arg Arg Lys Pro Trp
360                 365                 370                 375

GAG CTG GAC TGC CAG GTG GAC ATC GCC TTC CCC TGC GCC ACC CAG AAC            1205
Glu Leu Asp Cys Gln Val Asp Ile Ala Phe Pro Cys Ala Thr Gln Asn
                380                 385                 390

GAG ATC GAT GAG CAC GAC GCC GAG CTG CTG ATC AAG CAC GGC TGC CAG            1253
Glu Ile Asp Glu His Asp Ala Glu Leu Leu Ile Lys His Gly Cys Gln
                395                 400                 405

TAC GTG GTG GAG GGC GCC AAC ATG CCC TCC ACC AAC GAG GCC ATC CAC            1301
Tyr Val Val Glu Gly Ala Asn Met Pro Ser Thr Asn Glu Ala Ile His
                410                 415                 420

AAG TAC AAC AAG GCC GGC ATC ATC TAC TGC CCC GGC AAG GCG GCC AAC            1349
```

```
Lys Tyr Asn Lys Ala Gly Ile Ile Tyr Cys Pro Gly Lys Ala Ala Asn
    425                 430                 435

GCC GGC GGC GTG GCG GTC AGC GGC CTG GAG ATG ACC CAG AAC CGC ATG      1397
Ala Gly Gly Val Ala Val Ser Gly Leu Glu Met Thr Gln Asn Arg Met
440                 445                 450                 455

AGC CTG AAC TGG ACT CGC GAG GAG GTT CGC GAC AAG CTG GAG CGC ATC      1445
Ser Leu Asn Trp Thr Arg Glu Glu Val Arg Asp Lys Leu Glu Arg Ile
                460                 465                 470

ATG AAG GAC ATC TAC GAC TCC GCC ATG GGG CCG TCC CGC AGA TAC AAT      1493
Met Lys Asp Ile Tyr Asp Ser Ala Met Gly Pro Ser Arg Arg Tyr Asn
            475                 480                 485

GTT GAC CTG GCT GCG GGC GCC AAC ATC GCG GGC TTC ACC AAG GTG GCT      1541
Val Asp Leu Ala Ala Gly Ala Asn Ile Ala Gly Phe Thr Lys Val Ala
        490                 495                 500

GAT GCC GTC AAG GCC CAG GGC GCT GTT TAAGCTGCCC AGGCCCAAGC            1588
Asp Ala Val Lys Ala Gln Gly Ala Val
    505                 510

CACGGCTCAC CGGCAATCCA ACCCAACCAA CTCAACGGCC AGGACCTTTT CGGAAGCGGC    1648

GCCTTTTTCC CAGCCAGGGC CCTCACCTGC CCTTTCATAA CCCTGCTATT GCCGCCGTGC    1708

CCCTGCAATT CCACCCCAAG AAGAACTAGC GGCACTTGAC TGCATCAGGA CGGCTATTTT    1768

TTTCGCGACG CGCGCTCACC CCGAGAGCCT CTCTCCCCCG AGCCCTAAGC GCTGACGTCC    1828

GCCCGACTTT GCCTCGCACA TCGCTCGGTT TTGACCCCCT CCAGTCTACC CACCCTGTTG    1888

TGAAGCCTAC CAGCTCAATT GCCTTTTAGT GTATGTGCGC CCCCTCCTGC CCCGAATTT     1948

TCCTGCCATG AGACGTGCGG TTCCTAGCCT GGTGACCCCA AGTAGCAGTT AGTGTGCGTG    2008

CCTTGCCCTG CGCTGCCCGG GATGCGATAC TGTGACCTGA GAGTGCTTGT GTAAACACGA    2068

CGAGTCAAAA AAAAAAAAAA AAAAAAAAA A                                    2099

(2) INFORMATION FOR SEQ ID NO:4:

(i) SEQUENCE CHARACTERISTICS:
        (A) LENGTH: 512 amino acids
        (B) TYPE: amino acid
        (D) TOPOLOGY: linear (ii) MOLECULE TYPE: protein (xi) SEQUENCE DESCRIPTION: SEQ ID NO:4:

Met Gln Thr Ala Leu Val Ala Lys Pro Ile Val Ala Cys Ala Trp Val
1               5                   10                  15

Arg Ser Ala Lys Arg Asp Val Arg Ala Lys Ala Val Ser Leu Glu Glu
            20                  25                  30

Gln Ile Ser Ala Met Asp Ala Thr Thr Gly Asp Phe Thr Ala Leu Gln
        35                  40                  45

Lys Ala Val Lys Gln Met Ala Thr Lys Ala Gly Thr Glu Gly Leu Val
    50                  55                  60

His Gly Ile Lys Asn Pro Asp Val Arg Gln Leu Leu Thr Glu Ile Phe
65                  70                  75                  80

Met Lys Asp Pro Glu Gln Gln Glu Phe Met Gln Ala Val Arg Glu Val
                85                  90                  95

Ala Val Ser Leu Gln Pro Val Phe Glu Lys Arg Pro Glu Leu Leu Pro
            100                 105                 110

Ile Phe Lys Gln Ile Val Glu Pro Glu Arg Val Ile Thr Phe Arg Val
        115                 120                 125

Ser Trp Leu Asp Asp Ala Gly Asn Leu Gln Val Asn Arg Gly Phe Arg
    130                 135                 140
```

```
Val Gln Tyr Ser Ser Ala Ile Gly Pro Tyr Lys Gly Gly Leu Arg Phe
145                 150                 155                 160

His Pro Ser Val Asn Leu Ser Ile Met Lys Phe Leu Ala Phe Glu Gln
            165                 170                 175

Ile Phe Lys Asn Ser Leu Thr Thr Leu Pro Met Gly Gly Lys Gly
            180                 185                 190

Gly Ser Asp Phe Asp Pro Lys Gly Lys Ser Asp Ala Glu Val Met Arg
        195                 200                 205

Phe Cys Gln Ser Phe Met Thr Glu Leu Gln Arg His Ile Ser Tyr Val
    210                 215                 220

Gln Asp Val Pro Ala Gly Asp Ile Gly Val Gly Ala Arg Glu Ile Gly
225                 230                 235                 240

Tyr Leu Phe Gly Gln Tyr Lys Arg Ile Thr Lys Asn Tyr Thr Gly Val
            245                 250                 255

Leu Thr Pro Lys Gly Gln Glu Tyr Gly Gly Ser Glu Ile Arg Pro Glu
            260                 265                 270

Ala Thr Gly Tyr Gly Ala Val Leu Phe Val Glu Asn Val Leu Lys Asp
            275                 280                 285

Lys Gly Glu Ser Leu Lys Gly Lys Arg Cys Leu Val Ser Gly Ala Gly
            290                 295                 300

Asn Val Ala Gln Tyr Cys Ala Glu Leu Leu Leu Glu Lys Gly Ala Ile
305                 310                 315                 320

Val Leu Ser Leu Ser Asp Ser Gln Gly Tyr Val Tyr Glu Pro Asn Gly
            325                 330                 335

Phe Thr Arg Glu Gln Leu Gln Ala Val Gln Asp Met Lys Lys Lys Asn
            340                 345                 350

Asn Ser Ala Arg Ile Ser Glu Tyr Lys Ser Asp Thr Ala Val Tyr Val
            355                 360                 365

Gly Asp Arg Arg Lys Pro Trp Glu Leu Asp Cys Gln Val Asp Ile Ala
370                 375                 380

Phe Pro Cys Ala Thr Gln Asn Glu Ile Asp Glu His Asp Ala Glu Leu
385                 390                 395                 400

Leu Ile Lys His Gly Cys Gln Tyr Val Val Glu Gly Ala Asn Met Pro
            405                 410                 415

Ser Thr Asn Glu Ala Ile His Lys Tyr Asn Lys Ala Gly Ile Ile Tyr
            420                 425                 430

Cys Pro Gly Lys Ala Ala Asn Ala Gly Gly Val Ala Val Ser Gly Leu
            435                 440                 445

Glu Met Thr Gln Asn Arg Met Ser Leu Asn Trp Thr Arg Glu Glu Val
            450                 455                 460

Arg Asp Lys Leu Glu Arg Ile Met Lys Asp Ile Tyr Asp Ser Ala Met
465                 470                 475                 480

Gly Pro Ser Arg Arg Tyr Asn Val Asp Leu Ala Ala Gly Ala Asn Ile
            485                 490                 495

Ala Gly Phe Thr Lys Val Ala Asp Ala Val Lys Ala Gln Gly Ala Val
            500                 505                 510
```

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ala Val Ser Leu Glu Glu Gln Ile Ser Ala Met Asp Ala Thr Thr Gly
1               5                   10                  15

Asp Phe Thr Ala
            20

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Asp Ala Thr Thr Gly Asp Phe Thr Ala Leu
1               5                   10

(2) INFORMATION FOR SEQ ID NO:7:

(i) SEQUENCE CHARACTERISTICS:
        (A) LENGTH: 1969 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

```
CAGATCTCCG CGATGGACGC CACCACCGGC GACTTCACGG CGCTGCAGAA GGCGGTGAAG      60
CAGATGGCCA CCAAGGCGGG CACTGAGGGC CTGGTGCACG GCATCAAGAA CCCCGACGTG     120
CGCCAGCTGC TGACCGAGAT CTTCATGAAG GACCCGGAGC AGCAGGAGTT CATGCAGGCG     180
GTGCGCGAGG TGGCCGTCTC CCTGCAGCCC GTGTTCGAGA AGCGCCCCGA GCTGCTGCCC     240
ATCTTCAAGC AGATCGTTGA GCCTGAGCGC GTGATCACCT TCCGCGTGTC CTGGCTGGAC     300
GACGCCGGCA ACCTGCAGGT CAACCGCGGC TTCCGCGTGC AGTACTCGTC CGCCATCGGC     360
CCCTACAAGG GCGGCCTGCG CTTCCACCCC TCCGTGAACC TGTCCATCAT GAAGTTCCTT     420
GCCTTTGAGC AGATCTTCAA GAACAGCCTG ACCACCCTGC CCATGGGCGG CGGCAAGGGC     480
GGCTCCGACT TCGACCCCAA GGGCAAGAGC GACGCGGAGG TGATGCGCTT CTGCCAGTCC     540
TTCATGACCG AGCTGCAGCG CCACATCAGC TACGTGCAGG ACGTGCCCGC CGGCGACATC     600
GGCGTGGGCG CGCGCGAGAT TGGCTACCTT TTCGGCCAGT ACAAGCGCAT CACCAAGAAC     660
TACACCGGCG TGCTGACCCC GAAGGGCCAG GAGTATGGCG GCTCCGAGAT CCGCCCCGAG     720
GCCACCGGCT ACGGCGCCGT GCTGTTTGTG GAGAACGTGC TGAAGGACAA GGGCGAGAGC     780
CTCAAGGGCA AGCGCTGCCT GGTGTCTGGC GCGGGCAACG TGGCCCAGTA CTGCGCGGAG     840
CTGCTGCTGG AGAAGGGCGC CATCGTGCTG TCGCTGTCCG ACTCCCAGGG CTACGTGTAC     900
GAGCCCAACG GCTTCACGCG CGAGCAGCTG CAGGCGGTGC AGGACATGAA GAAGAAGAAC     960
AACAGCGCCC GCATCTCCGA GTACAAGAGC GACACCGCCG TGTATGTGGG CGACCGCCGC    1020
AAGCCTTGGG AGCTGGACTG CCAGGTGGAC ATCGCCTTCC CCTGCGCCAC CCAGAACGAG    1080
ATCGATGAGC ACGACGCCGA GCTGCTGATC AAGCACGGCT GCCAGTACGT GGTGGAGGGC    1140
GCCAACATGC CCTCCACCAA CGAGGCCATC CACAAGTACA ACAAGGCGGG CATCATCTAC    1200
TGCCCCGGCA AGGCGGCCAA CGCCGGCGGC GTGGCGGTCA GCGGCCTGGA GATGACCCAG    1260
AACCGCATGA GCCTGAACTG GACTCGCGAG GAGGTTCGCG ACAAGCTGGA GCGCATCATG    1320
```

```
AAGGACATCT ACGACTCCGC CATGGGGCCG TCCCGCAGAT ACAATGTTGA CCTGGCTGCG    1380

GGCGCCAACA TCGCGGGCTT CACCAAGGTG GCTGATGCCG TCAAGGCCCA GGGCGCTGTT    1440

TAAGCTGCCC AGGCCCAAGC CACGGCTCAC CGGCAATCCA ACCCAACCAA CTCAACGGCC    1500

AGGACCTTTT CGGAAGCGGC GCCTTTTTCC CAGCCAGGGC CCTCACCTGC CCTTTCATAA    1560

CCCTGCTATT GCCGCCGTGC CCCTGCAATT CCACCCCAAG AAGAACTAGC GGCACTTGAC    1620

TGCATCAGGA CGGCTATTTT TTTCGCGACG CGCGCTCACC CCGAGAGCCT CTCTCCCCCG    1680

AGCCCTAAGC GCTGACGTCC GCCCGACTTT GCCTCGCACA TCGCTCGGTT TTGACCCCCT    1740

CCAGTCTACC CACCCTGTTG TGAAGCCTAC CAGCTCAATT GCCTTTTAGT GTATGTGCGC    1800

CCCCTCCTGC CCCCGAATTT TCCTGCCATG AGACGTGCGG TTCCTAGCCT GGTGACCCCA    1860

AGTAGCAGTT AGTGTGCGTG CCTTGCCCTG CGCTGCCCGG GATGCGATAC TGTGACCTGA    1920

GAGTGCTTGT GTAAACACGA CGAGTCAAAA AAAAAAAAAA AAAAAAAA               1969

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

CTCAAAGGCA AGGAACTTCA TG                                             22

(2) INFORMATION FOR SEQ ID NO:9:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

GGGTCGACAT TCTAGACAGA ATTCGTGGAT CCTTTTTTTT TTTTTTTTT                50

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

GGACGAGTAC TGCACGC                                                   17

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO:11:
```

```
GATCTCGGTC AGCAGCTG                                                       18

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO:12:

GGGTCGACAT TCTAGACAGA A                                                   21

(2) INFORMATION FOR SEQ ID NO:13:

(i) SEQUENCE CHARACTERISTICS:
        (A) LENGTH: 367 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO:13:

GGGTCGACAT TCTAGACAGA ATTCGTGGAT CCTTTTTTTT TTTTTTTTTT TTTTTTCTCC         60

TTTCTGCTCG CCCTCTCTCC GTCCCGCCAT GCAGACCGCC CTCGTCGCCA AGCCTATCGT        120

GGCCGCCCCG CTGGCGGCAC GCCCGCGCTG CCTCGCGCCG TGGCCGTGCG CGTGGGTCCG        180

CTCCGCCAAG CGCGATGTCC GCGCCAAGGC CGTCTCGCTG GAGGAGCAGA TCTCCGCGAT        240

GGACGCCACC ACCGGCGACT TCACGGCGCT GCAGAAGGCG GTGAAGCAGA TGGCCACCAA        300

GGCGGGCACT GAGGGCCTGG TGCACGGCAT CAAGAACCCC GACGTGCGCC AGCTGCTGAC        360

CGAGATC                                                                  367

(2) INFORMATION FOR SEQ ID NO:14:

(i) SEQUENCE CHARACTERISTICS:
        (A) LENGTH: 325 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO:14:

GGGTCGACAT TCTAGACAGA ATTCGTGGAT CCTTTTTTTT TTTTTTTTTT TTTTTTCTCC         60

TTTCTGCTCG CCCTCTCTCC GTCCCGCCAT GCAGACCGCC CTCGTCGCCA AGCCTATCGT        120

GGCCTGCGCG TGGGTCCGCT CCGCCAAGCG CGATGTCCGC GCCAAGGCCG TCTCGCTGGA        180

GGAGCAGATC TCCGCGATGG ACGCCACCAC CGGCGACTTC ACGGCGCTGC AGAAGGCGGT        240

GAAGCAGATG GCCACCAAGG CGGGCACTGA GGGCCTGGTG CACGGCATCA AGAACCCCGA        300

CGTGCGCCAG CTGCTGACCG AGATC                                              325

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: CDNA
```

(xi) SEQUENCE DESCRIPTION: SEQ ID NO:15:

CTTTCTGCTC GCCCTCTC                                                    18

(2) INFORMATION FOR SEQ ID NO:16:

(i) SEQUENCE CHARACTERISTICS:
        (A) LENGTH: 308 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO:16:

CTTTCTGCTC GCCCTCTCTC CGTCCCGCCA TGCAGACCGC CCTCGTCGCC AAGCCTATCG      60

TGGCCGCCCC GCTGGCGGCA CGCCCGCGCT GCCTCGCGCC GTGGCCGTGC GCGTGGGTCC     120

GCTCCGCCAA GCGCGATGTC CGCGCCAAGG CCGTCTCGCT GGAGGAGCAG ATCTCCGCGA     180

TGGACGCCAC CACCGGCGAC TTCACGGCGC TGCAGAAGGC GGTGAAGCAG ATGGCCACCA     240

AGGCGGGCAC TGAGGGCCTG GTGCACGGCA TCAAGAACCC CGACGTGCGC CAGCTGCTGA     300

CCGAGATC                                                             308

(2) INFORMATION FOR SEQ ID NO:17:

(i) SEQUENCE CHARACTERISTICS:
        (A) LENGTH: 266 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO:17:

CTTTCTGCTC GCCCTCTCTC CGTCCCGCCA TGCAGACCGC CCTCGTCGCC AAGCCTATCG      60

TGGCCTGCGC GTGGGTCCGC TCCGCCAAGC GCGATGTCCG CGCCAAGGCC GTCTCGCTGG     120

AGGAGCAGAT CTCCGCGATG GACGCCACCA CCGGCGACTT CACGGCGCTG CAGAAGGCGG     180

TGAAGCAGAT GGCCACCAAG GCGGGCACTG AGGGCCTGGT GCACGGCATC AAGAACCCCG     240

ACGTGCGCCA GCTGCTGACC GAGATC                                         266

(2) INFORMATION FOR SEQ ID NO:18:

(i) SEQUENCE CHARACTERISTICS:
        (A) LENGTH: 2137 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO:18:

CTTTCTGCTC GCCCTCTCTC CGTCCCGCCA TGCAGACCGC CCTCGTCGCC AAGCCTATCG      60

TGGCCGCCCC GCTGGCGGCA CGCCCGCGCT GCCTCGCGCC GTGGCCGTGC GCGTGGGTCC     120

GCTCCGCCAA GCGCGATGTC CGCGCCAAGG CCGTCTCGCT GGAGGAGCAG ATCTCCGCGA     180

TGGACGCCAC CACCGGCGAC TTCACGGCGC TGCAGAAGGC GGTGAAGCAG ATGGCCACCA     240

AGGCGGGCAC TGAGGGCCTG GTGCACGGCA TCAAGAACCC CGACGTGCGC CAGCTGCTGA     300

CCGAGATCTT CATGAAGGAC CCGGAGCAGC AGGAGTTCAT GCAGGCGGTG CGCGAGGTGG     360

CCGTCTCCCT GCAGCCCGTG TTCGAGAAGC GCCCCGAGCT GCTGCCCATC TTCAAGCAGA     420

```
TCGTTGAGCC TGAGCGCGTG ATCACCTTCC GCGTGTCCTG GCTGGACGAC GCCGGCAACC    480

TGCAGGTCAA CCGCGGCTTC CGCGTGCAGT ACTCGTCCGC CATCGGCCCC TACAAGGGCG    540

GCCTGCGCTT CCACCCCTCC GTGAACCTGT CCATCATGAA GTTCCTTGCC TTTGAGCAGA    600

TCTTCAAGAA CAGCCTGACC ACCCTGCCCA TGGGCGGCGG CAAGGGCGGC TCCGACTTCG    660

ACCCCAAGGG CAAGAGCGAC GCGGAGGTGA TGCGCTTCTG CCAGTCCTTC ATGACCGAGC    720

TGCAGCGCCA CATCAGCTAC GTGCAGGACG TGCCCGCCGG CGACATCGGC GTGGGCGCGC    780

GCGAGATTGG CTACCTTTTC GGCCAGTACA AGCGCATCAC CAAGAACTAC ACCGGCGTGC    840

TGACCCCGAA GGGCCAGGAG TATGGCGGCT CCGAGATCCG CCCCGAGGCC ACCGGCTACG    900

GCGCCGTGCT GTTTGTGGAG AACGTGCTGA AGGACAAGGG CGAGAGCCTC AAGGGCAAGC    960

GCTGCCTGGT GTCTGGCGCG GGCAACGTGG CCCAGTACTG CGCGGAGCTG CTGCTGGAGA   1020

AGGGCGCCAT CGTGCTGTCG CTGTCCGACT CCCAGGGCTA CGTGTACGAG CCCAACGGCT   1080

TCACGCGCGA GCAGCTGCAG GCGGTGCAGG ACATGAAGAA GAAGAACAAC AGCGCCCGCA   1140

TCTCCGAGTA CAAGAGCGAC ACCGCCGTGT ATGTGGGCGA CCGCCGCAAG CCTTGGGAGC   1200

TGGACTGCCA GGTGGACATC GCCTTCCCCT GCGCCACCCA GAACGAGATC GATGAGCACG   1260

ACGCCGAGCT GCTGATCAAG CACGGCTGCC AGTACGTGGT GGAGGGCGCC AACATGCCCT   1320

CCACCAACGA GGCCATCCAC AAGTACAACA AGGCCGGCAT CATCTACTGC CCCGGCAAGG   1380

CGGCCAACGC CGGCGGCGTG GCGGTCAGCG GCCTGGAGAT GACCCAGAAC CGCATGAGCC   1440

TGAACTGGAC TCGCGAGGAG GTTCGCGACA GCTGGAGCG CATCATGAAG GACATCTACG   1500

ACTCCGCCAT GGGGCCGTCC CGCAGATACA ATGTTGACCT GGCTGCGGGC GCCAACATCG   1560

CGGGCTTCAC CAAGGTGGCT GATGCCGTCA AGGCCCAGGG CGCTGTTTAA GCTGCCCAGG   1620

CCCAAGCCAC GGCTCACCGG CAATCCAACC CAACCAACTC AACGGCCAGG ACCTTTTCGG   1680

AAGCGGCGCC TTTTTCCCAG CCAGGGCCCT CACCTGCCCT TTCATAACCC TGCTATTGCC   1740

GCCGTGCCCC TGCAATTCCA CCCCAAGAAG AACTAGCGGC ACTTGACTGC ATCAGGACGG   1800

CTATTTTTTT CGCGACGCGC GCTCACCCCG AGAGCCTCTC TCCCCCGAGC CCTAAGCGCT   1860

GACGTCCGCC CGACTTTGCC TCGCACATCG CTCGGTTTTG ACCCCCTCCA GTCTACCCAC   1920

CCTGTTGTGA AGCCTACCAG CTCAATTGCC TTTTAGTGTA TGTGCGCCCC CTCCTGCCCC   1980

CGAATTTTCC TGCCATGAGA CGTGCGGTTC CTAGCCTGGT GACCCCAAGT AGCAGTTAGT   2040

GTGCGTGCCT TGCCCTGCGC TGCCCGGGAT GCGATACTGT GACCTGAGAG TGCTTGTGTA   2100

AACACGACGA GTCAAAAAAA AAAAAAAAAA AAAAAA                             2137

(2) INFORMATION FOR SEQ ID NO:19:

(i) SEQUENCE CHARACTERISTICS:
        (A) LENGTH: 2096 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO:19:

CTTTCTGCTC GCCCTCTCTC CGTCCCGCCA TGCAGACCGC CCTCGTCGCC AAGCCTATCG     60

TGGCCTGCGC GTGGGTCCGC TCCGCCAAGC GCGATGTCCG CGCCAAGGCC GTCTCGCTGG    120

AGGAGCAGAT CTCGCGATG GACGCCACCA CCGGCGACTT CACGGCGCTG CAGAAGGCGG    180

TGAAGCAGAT GGCCACCAAG GCGGGCACTG AGGGCCTGGT GCACGGCATC AAGAACCCCG    240

ACGTGCGCCA GCTGCTGACC GAGATCTTCA TGAAGGACCC GGAGCAGCAG GAGTTCATGC    300
```

```
AGGCGGTGCG CGAGGTGGCC GTCTCCCTGC AGCCCGTGTT CGAGAAGCGC CCCGAGCTGC    360

TGCCCATCTT CAAGCAGATC GTTGAGCCTG AGCGCGTGAT CACCTTCCGC GTGTCCTGGC    420

TGGACGACGC CGGCAACCTG CAGGTCAACC GCGGCTTCCG CGTGCAGTAC TCGTCCGCCA    480

TCGGCCCCTA CAAGGGCGGC CTGCGCTTCC ACCCCTCCGT GAACCTGTCC ATCATGAAGT    540

TCCTTGCCTT TGAGCAGATC TTCAAGAACA GCCTGACCAC CCTGCCCATG GGCGGCGGCA    600

AGGGCGGCTC CGACTTCGAC CCCAAGGGCA AGAGCGACGC GGAGGTGATG CGCTTCTGCC    660

AGTCCTTCAT GACCGAGCTG CAGCGCCACA TCAGCTACGT GCAGGACGTG CCCGCCGGCG    720

ACATCGGCGT GGGCGCGCGC GAGATTGGCT ACCTTTTCGG CCAGTACAAG CGCATCACCA    780

AGAACTACAC CGGCGTGCTG ACCCCGAAGG GCCAGGAGTA TGGCGGCTCC GAGATCCGCC    840

CCGAGGCCAC CGGCTACGGC GCCGTGCTGT TTGTGGAGAA CGTGCTGAAG GACAAGGGCG    900

AGAGCCTCAA GGGCAAGCGC TGCCTGGTGT CTGGCGCGGG CAACGTGGCC CAGTACTGCG    960

CGGAGCTGCT GCTGGAGAAG GGCGCCATCG TGCTGTCGCT GTCCGACTCC CAGGGCTACG    1020

TGTACGAGCC CAACGGCTTC ACGCGCGAGC AGCTGCAGGC GGTGCAGGAC ATGAAGAAGA    1080

AGAACAACAG CGCCCGCATC TCCGAGTACA AGAGCGACAC CGCCGTGTAT GTGGGCGACC    1140

GCCGCAAGCC TTGGGAGCTG GACTGCCAGG TGGACATCGC CTTCCCCTGC GCCACCCAGA    1200

ACGAGATCGA TGAGCACGAC GCCGAGCTGC TGATCAAGCA CGGCTGCCAG TACGTGGTGG    1260

AGGGCGCCAA CATGCCCTCC ACCAACGAGG CCATCCACAA GTACAACAAG GCCGGCATCA    1320

TCTACTGCCC CGGCAAGGCG GCCAACGCCG GCGGCGTGGC GGTCAGCGGC CTGGAGATGA    1380

CCCAGAACCG CATGAGCCTG AACTGGACTC GCGAGGAGGT TCGCGACAAG CTGGAGCGCA    1440

TCATGAAGGA CATCTACGAC TCCGCCATGG GGCCGTCCCG CAGATACAAT GTTGACCTGG    1500

CTGCGGGCGC CAACATCGCG GGCTTCACCA AGGTGGCTGA TGCCGTCAAG GCCCAGGGCG    1560

CTGTTTAAGC TGCCCAGGCC CAAGCCACGG CTCACCGGCA ATCCAACCCA ACCAACTCAA    1620

CGGCCAGGAC CTTTTCGGAA GCGGCGCCTT TTTCCCAGCC AGGGCCCTCA CCTGCCCTTT    1680

CATAACCCTG CTATTGCCGC CGTGCCCCTG CAATTCCACC CCAAGAAGAA CTAGCGGCAC    1740

TTGACTGCAT CAGGACGGCT ATTTTTTTCG CGACGCGCGC TCACCCCGAG AGCCTCTCTC    1800

CCCCGAGCCC TAAGCGCTGA CGTCCGCCCG ACTTTGCCTC GCACATCGCT CGGTTTTGAC    1860

CCCCTCCAGT CTACCCACCC TGTTGTGAAG CCTACCAGCT CAATTGCCTT TTAGTGTATG    1920

TGCGCCCCCT CCTGCCCCCG AATTTTCCTG CCATGAGACG TGCGGTTCCT AGCCTGGTGA    1980

CCCCAAGTAG CAGTTAGTGT GCGTGCCTTG CCCTGCGCTG CCCGGGATGC GATACTGTGA    2040

CCTGAGAGTG CTTGTGTAAA CACGACGAGT CAAAAAAAAA AAAAAAAAAA AAAAAA        2096
```

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:20:

```
CATATGGCCG TCTCGCTGGG AGGAG                                            25
```

(2) INFORMATION FOR SEQ ID NO:21:

(i) SEQUENCE CHARACTERISTICS:

-continued (A) LENGTH: 19 base pairs
(B) TYPE: nucleic acid
(C) STRANDEDNESS: double
(D) TOPOLOGY: linear (ii) MOLECULE TYPE: CDNA (xi) SEQUENCE DESCRIPTION: SEQ ID NO:21:

GTTGGATTGC CGGTGAGCC                                                          19

(2) INFORMATION FOR SEQ ID NO:22:

(i) SEQUENCE CHARACTERISTICS:
(A) LENGTH: 21 base pairs
(B) TYPE: nucleic acid
(C) STRANDEDNESS: double
(D) TOPOLOGY: linear (ii) MOLECULE TYPE: CDNA (xi) SEQUENCE DESCRIPTION: SEQ ID NO:22:

CATATGGACG CCACCACCGG C                                                       21

(2) INFORMATION FOR SEQ ID NO:23:

(i) SEQUENCE CHARACTERISTICS:
(A) LENGTH: 1506 base pairs
(B) TYPE: nucleic acid
(C) STRANDEDNESS: double
(D) TOPOLOGY: linear (ii) MOLECULE TYPE: CDNA (ix) FEATURE:
(A) NAME/KEY: CDS
(B) LOCATION: 4..1464

(xi) SEQUENCE DESCRIPTION: SEQ ID NO:23:

```
CAT ATG GCC GTC TCG CTG GAG GAG CAG ATC TCC GCG ATG GAC GCC ACC              48
    Met Ala Val Ser Leu Glu Glu Gln Ile Ser Ala Met Asp Ala Thr
        515                 520                 525

ACC GGC GAC TTC ACG GCG CTG CAG AAG GCG GTG AAG CAG ATG GCC ACC              96
Thr Gly Asp Phe Thr Ala Leu Gln Lys Ala Val Lys Gln Met Ala Thr
            530                 535                 540

AAG GCG GGC ACT GAG GGC CTG GTG CAC GGC ATC AAG AAC CCC GAC GTG             144
Lys Ala Gly Thr Glu Gly Leu Val His Gly Ile Lys Asn Pro Asp Val
545                 550                 555

CGC CAG CTG CTG ACC GAG ATC TTC ATG AAG GAC CCG GAG CAG CAG GAG             192
Arg Gln Leu Leu Thr Glu Ile Phe Met Lys Asp Pro Glu Gln Gln Glu
560                 565                 570                 575

TTC ATG CAG GCG GTG CGC GAG GTG GCC GTC TCC CTG CAG CCC GTG TTC             240
Phe Met Gln Ala Val Arg Glu Val Ala Val Ser Leu Gln Pro Val Phe
            580                 585                 590

GAG AAG CGC CCC GAG CTG CTG CCC ATC TTC AAG CAG ATC GTT GAG CCT             288
Glu Lys Arg Pro Glu Leu Leu Pro Ile Phe Lys Gln Ile Val Glu Pro
            595                 600                 605

GAG CGC GTG ATC ACC TTC CGC GTG TCC TGG CTG GAC GAC GCC GGC AAC             336
Glu Arg Val Ile Thr Phe Arg Val Ser Trp Leu Asp Asp Ala Gly Asn
            610                 615                 620

CTG CAG GTC AAC CGC GGC TTC CGC GTG CAG TAC TCG TCC GCC ATC GGC             384
Leu Gln Val Asn Arg Gly Phe Arg Val Gln Tyr Ser Ser Ala Ile Gly
625                 630                 635

CCC TAC AAG GGC GGC CTG CGC TTC CAC CCC TCC GTG AAC CTG TCC ATC             432
Pro Tyr Lys Gly Gly Leu Arg Phe His Pro Ser Val Asn Leu Ser Ile
640                 645                 650                 655

ATG AAG TTC CTT GCC TTT GAG CAG ATC TTC AAG AAC AGC CTG ACC ACC             480
```

-continued

```
          Met Lys Phe Leu Ala Phe Glu Gln Ile Phe Lys Asn Ser Leu Thr Thr
                      660                 665                 670

CTG CCC ATG GGC GGC GGC AAG GGC GGC TCC GAC TTC GAC CCC AAG GGC                528
Leu Pro Met Gly Gly Gly Lys Gly Gly Ser Asp Phe Asp Pro Lys Gly
            675                 680                 685

AAG AGC GAC GCG GAG GTG ATG CGC TTC TGC CAG TCC TTC ATG ACC GAG                576
Lys Ser Asp Ala Glu Val Met Arg Phe Cys Gln Ser Phe Met Thr Glu
        690                 695                 700

CTG CAG CGC CAC ATC AGC TAC GTG CAG GAC GTG CCC GCC GGC GAC ATC                624
Leu Gln Arg His Ile Ser Tyr Val Gln Asp Val Pro Ala Gly Asp Ile
    705                 710                 715

GGC GTG GGC GCG CGC GAG ATT GGC TAC CTT TTC GGC CAG TAC AAG CGC                672
Gly Val Gly Ala Arg Glu Ile Gly Tyr Leu Phe Gly Gln Tyr Lys Arg
720                 725                 730                 735

ATC ACC AAG AAC TAC ACC GGC GTG CTG ACC CCG AAG GGC CAG GAG TAT                720
Ile Thr Lys Asn Tyr Thr Gly Val Leu Thr Pro Lys Gly Gln Glu Tyr
                740                 745                 750

GGC GGC TCC GAG ATC CGC CCC GAG GCC ACC GGC TAC GGC GCC GTG CTG                768
Gly Gly Ser Glu Ile Arg Pro Glu Ala Thr Gly Tyr Gly Ala Val Leu
            755                 760                 765

TTT GTG GAG AAC GTG CTG AAG GAC AAG GGC GAG AGC CTC AAG GGC AAG                816
Phe Val Glu Asn Val Leu Lys Asp Lys Gly Glu Ser Leu Lys Gly Lys
        770                 775                 780

CGC TGC CTG GTG TCT GGC GCG GGC AAC GTG GCC CAG TAC TGC GCG GAG                864
Arg Cys Leu Val Ser Gly Ala Gly Asn Val Ala Gln Tyr Cys Ala Glu
    785                 790                 795

CTG CTG CTG GAG AAG GGC GCC ATC GTG CTG TCG CTG TCC GAC TCC CAG                912
Leu Leu Leu Glu Lys Gly Ala Ile Val Leu Ser Leu Ser Asp Ser Gln
800                 805                 810                 815

GGC TAC GTG TAC GAG CCC AAC GGC TTC ACG CGC GAG CAG CTG CAG GCG                960
Gly Tyr Val Tyr Glu Pro Asn Gly Phe Thr Arg Glu Gln Leu Gln Ala
                820                 825                 830

GTG CAG GAC ATG AAG AAG AAG AAC AAC AGC GCC CGC ATC TCC GAG TAC               1008
Val Gln Asp Met Lys Lys Lys Asn Asn Ser Ala Arg Ile Ser Glu Tyr
            835                 840                 845

AAG AGC GAC ACC GCC GTG TAT GTG GGC GAC CGC CGC AAG CCT TGG GAG               1056
Lys Ser Asp Thr Ala Val Tyr Val Gly Asp Arg Arg Lys Pro Trp Glu
        850                 855                 860

CTG GAC TGC CAG GTG GAC ATC GCC TTC CCC TGC GCC ACC CAG AAC GAG               1104
Leu Asp Cys Gln Val Asp Ile Ala Phe Pro Cys Ala Thr Gln Asn Glu
    865                 870                 875

ATC GAT GAG CAC GAC GCC GAG CTG CTG ATC AAG CAC GGC TGC CAG TAC               1152
Ile Asp Glu His Asp Ala Glu Leu Leu Ile Lys His Gly Cys Gln Tyr
880                 885                 890                 895

GTG GTG GAG GGC GCC AAC ATG CCC TCC ACC AAC GAG GCC ATC CAC AAG               1200
Val Val Glu Gly Ala Asn Met Pro Ser Thr Asn Glu Ala Ile His Lys
                900                 905                 910

TAC AAC AAG GCC GGC ATC ATC TAC TGC CCC GGC AAG GCG GCC AAC GCC               1248
Tyr Asn Lys Ala Gly Ile Ile Tyr Cys Pro Gly Lys Ala Ala Asn Ala
            915                 920                 925

GGC GGC GTG GCG GTC AGC GGC CTG GAG ATG ACC CAG AAC CGC ATG AGC               1296
Gly Gly Val Ala Val Ser Gly Leu Glu Met Thr Gln Asn Arg Met Ser
        930                 935                 940

CTG AAC TGG ACT CGC GAG GAG GTT CGC GAC AAG CTG GAG CGC ATC ATG               1344
Leu Asn Trp Thr Arg Glu Glu Val Arg Asp Lys Leu Glu Arg Ile Met
    945                 950                 955

AAG GAC ATC TAC GAC TCC GCC ATG GGG CCG TCC CGC AGA TAC AAT GTT               1392
Lys Asp Ile Tyr Asp Ser Ala Met Gly Pro Ser Arg Arg Tyr Asn Val
960                 965                 970                 975

GAC CTG GCT GCG GGC GCC AAC ATC GCG GGC TTC ACC AAG GTG GCT GAT               1440
```

```
Asp Leu Ala Ala Gly Ala Asn Ile Ala Gly Phe Thr Lys Val Ala Asp
            980                 985                 990

GCC GTC AAG GCC CAG GGC GCT GTT TAAGCTGCCC AGGCCCAAGC CACGGCTCAC    1494
Ala Val Lys Ala Gln Gly Ala Val
            995

CGGCAATCCA AC                                                       1506
```

(2) INFORMATION FOR SEQ ID NO:24:

(i) SEQUENCE CHARACTERISTICS:
        (A) LENGTH: 487 amino acids
        (B) TYPE: amino acid
        (D) TOPOLOGY: linear (ii) MOLECULE TYPE: protein (xi) SEQUENCE DESCRIPTION: SEQ ID NO:24:

```
Met Ala Val Ser Leu Glu Glu Gln Ile Ser Ala Met Asp Ala Thr Thr
 1               5                  10                  15

Gly Asp Phe Thr Ala Leu Gln Lys Ala Val Lys Gln Met Ala Thr Lys
            20                  25                  30

Ala Gly Thr Glu Gly Leu Val His Gly Ile Lys Asn Pro Asp Val Arg
        35                  40                  45

Gln Leu Leu Thr Glu Ile Phe Met Lys Asp Pro Glu Gln Gln Glu Phe
    50                  55                  60

Met Gln Ala Val Arg Glu Val Ala Val Ser Leu Gln Pro Val Phe Glu
65                  70                  75                  80

Lys Arg Pro Glu Leu Leu Pro Ile Phe Lys Gln Ile Val Glu Pro Glu
                85                  90                  95

Arg Val Ile Thr Phe Arg Val Ser Trp Leu Asp Asp Ala Gly Asn Leu
            100                 105                 110

Gln Val Asn Arg Gly Phe Arg Val Gln Tyr Ser Ser Ala Ile Gly Pro
        115                 120                 125

Tyr Lys Gly Gly Leu Arg Phe His Pro Ser Val Asn Leu Ser Ile Met
    130                 135                 140

Lys Phe Leu Ala Phe Glu Gln Ile Phe Lys Asn Ser Leu Thr Thr Leu
145                 150                 155                 160

Pro Met Gly Gly Gly Lys Gly Gly Ser Asp Phe Asp Pro Lys Gly Lys
                165                 170                 175

Ser Asp Ala Glu Val Met Arg Phe Cys Gln Ser Phe Met Thr Glu Leu
            180                 185                 190

Gln Arg His Ile Ser Tyr Val Gln Asp Val Pro Ala Gly Asp Ile Gly
        195                 200                 205

Val Gly Ala Arg Glu Ile Gly Tyr Leu Phe Gly Gln Tyr Lys Arg Ile
    210                 215                 220

Thr Lys Asn Tyr Thr Gly Val Leu Thr Pro Lys Gly Gln Glu Tyr Gly
225                 230                 235                 240

Gly Ser Glu Ile Arg Pro Glu Ala Thr Gly Tyr Gly Ala Val Leu Phe
                245                 250                 255

Val Glu Asn Val Leu Lys Asp Lys Gly Glu Ser Leu Lys Gly Lys Arg
            260                 265                 270

Cys Leu Val Ser Gly Ala Gly Asn Val Ala Gln Tyr Cys Ala Glu Leu
        275                 280                 285

Leu Leu Glu Lys Gly Ala Ile Val Leu Ser Leu Ser Asp Ser Gln Gly
    290                 295                 300

Tyr Val Tyr Glu Pro Asn Gly Phe Thr Arg Glu Gln Leu Gln Ala Val
305                 310                 315                 320
```

```
Gln Asp Met Lys Lys Asn Asn Ser Ala Arg Ile Ser Glu Tyr Lys
            325                 330                 335

Ser Asp Thr Ala Val Tyr Val Gly Asp Arg Arg Lys Pro Trp Glu Leu
            340                 345                 350

Asp Cys Gln Val Asp Ile Ala Phe Pro Cys Ala Thr Gln Asn Glu Ile
            355                 360                 365

Asp Glu His Asp Ala Glu Leu Leu Ile Lys His Gly Cys Gln Tyr Val
370                 375                 380

Val Glu Gly Ala Asn Met Pro Ser Thr Asn Glu Ala Ile His Lys Tyr
385                 390                 395                 400

Asn Lys Ala Gly Ile Ile Tyr Cys Pro Gly Lys Ala Ala Asn Ala Gly
            405                 410                 415

Gly Val Ala Val Ser Gly Leu Glu Met Thr Gln Asn Arg Met Ser Leu
            420                 425                 430

Asn Trp Thr Arg Glu Glu Val Arg Asp Lys Leu Glu Arg Ile Met Lys
            435                 440                 445

Asp Ile Tyr Asp Ser Ala Met Gly Pro Ser Arg Arg Tyr Asn Val Asp
450                 455                 460

Leu Ala Ala Gly Ala Asn Ile Ala Gly Phe Thr Lys Val Ala Asp Ala
465                 470                 475                 480

Val Lys Ala Gln Gly Ala Val
            485

(2) INFORMATION FOR SEQ ID NO:25:

(i) SEQUENCE CHARACTERISTICS:
        (A) LENGTH: 1473 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 4..1431

(xi) SEQUENCE DESCRIPTION: SEQ ID NO:25:

CAT ATG GAC GCC ACC ACC GGC GAC TTC ACG GCG CTG CAG AAG GCG GTG        48
    Met Asp Ala Thr Thr Gly Asp Phe Thr Ala Leu Gln Lys Ala Val
            490                 495                 500

AAG CAG ATG GCC ACC AAG GCG GGC ACT GAG GGC CTG GTG CAC GGC ATC        96
Lys Gln Met Ala Thr Lys Ala Gly Thr Glu Gly Leu Val His Gly Ile
            505                 510                 515

AAG AAC CCC GAC GTG CGC CAG CTG CTG ACC GAG ATC TTC ATG AAG GAC       144
Lys Asn Pro Asp Val Arg Gln Leu Leu Thr Glu Ile Phe Met Lys Asp
520                 525                 530

CCG GAG CAG CAG GAG TTC ATG CAG GCG GTG CGC GAG GTG GCC GTC TCC       192
Pro Glu Gln Gln Glu Phe Met Gln Ala Val Arg Glu Val Ala Val Ser
535                 540                 545                 550

CTG CAG CCC GTG TTC GAG AAG CGC CCC GAG CTG CTG CCC ATC TTC AAG       240
Leu Gln Pro Val Phe Glu Lys Arg Pro Glu Leu Leu Pro Ile Phe Lys
            555                 560                 565

CAG ATC GTT GAG CCT GAG CGC GTG ATC ACC TTC CGC GTG TCC TGG CTG       288
Gln Ile Val Glu Pro Glu Arg Val Ile Thr Phe Arg Val Ser Trp Leu
            570                 575                 580

GAC GAC GCC GGC AAC CTG CAG GTC AAC CGC GGC TTC CGC GTG CAG TAC       336
Asp Asp Ala Gly Asn Leu Gln Val Asn Arg Gly Phe Arg Val Gln Tyr
            585                 590                 595

TCG TCC GCC ATC GGC CCC TAC AAG GGC GGC CTG CGC TTC CAC CCC TCC       384
```

-continued

| | | | | | | | | | | | | | |
|---|---|---|---|---|---|---|---|---|---|---|---|---|---|
| Ser | Ser | Ala | Ile | Gly | Pro | Tyr | Lys | Gly | Gly | Leu | Arg | Phe | His | Pro | Ser |
| | 600 | | | | 605 | | | | | 610 | | | | | |

| GTG | AAC | CTG | TCC | ATC | ATG | AAG | TTC | CTT | GCC | TTT | GAG | CAG | ATC | TTC | AAG | 432 |
|---|---|---|---|---|---|---|---|---|---|---|---|---|---|---|---|---|
| Val | Asn | Leu | Ser | Ile | Met | Lys | Phe | Leu | Ala | Phe | Glu | Gln | Ile | Phe | Lys | |
| 615 | | | | | 620 | | | | | 625 | | | | | 630 | |

| AAC | AGC | CTG | ACC | ACC | CTG | CCC | ATG | GGC | GGC | GGC | AAG | GGC | GGC | TCC | GAC | 480 |
|---|---|---|---|---|---|---|---|---|---|---|---|---|---|---|---|---|
| Asn | Ser | Leu | Thr | Thr | Leu | Pro | Met | Gly | Gly | Gly | Lys | Gly | Gly | Ser | Asp | |
| | | | | 635 | | | | | 640 | | | | | 645 | | |

| TTC | GAC | CCC | AAG | GGC | AAG | AGC | GAC | GCG | GAG | GTG | ATG | CGC | TTC | TGC | CAG | 528 |
|---|---|---|---|---|---|---|---|---|---|---|---|---|---|---|---|---|
| Phe | Asp | Pro | Lys | Gly | Lys | Ser | Asp | Ala | Glu | Val | Met | Arg | Phe | Cys | Gln | |
| | | | 650 | | | | | 655 | | | | | 660 | | | |

| TCC | TTC | ATG | ACC | GAG | CTG | CAG | CGC | CAC | ATC | AGC | TAC | GTG | CAG | GAC | GTG | 576 |
|---|---|---|---|---|---|---|---|---|---|---|---|---|---|---|---|---|
| Ser | Phe | Met | Thr | Glu | Leu | Gln | Arg | His | Ile | Ser | Tyr | Val | Gln | Asp | Val | |
| | | 665 | | | | | 670 | | | | | 675 | | | | |

| CCC | GCC | GGC | GAC | ATC | GGC | GTG | GGC | GCG | CGC | GAG | ATT | GGC | TAC | CTT | TTC | 624 |
|---|---|---|---|---|---|---|---|---|---|---|---|---|---|---|---|---|
| Pro | Ala | Gly | Asp | Ile | Gly | Val | Gly | Ala | Arg | Glu | Ile | Gly | Tyr | Leu | Phe | |
| | 680 | | | | | 685 | | | | | 690 | | | | | |

| GGC | CAG | TAC | AAG | CGC | ATC | ACC | AAG | AAC | TAC | ACC | GGC | GTG | CTG | ACC | CCG | 672 |
|---|---|---|---|---|---|---|---|---|---|---|---|---|---|---|---|---|
| Gly | Gln | Tyr | Lys | Arg | Ile | Thr | Lys | Asn | Tyr | Thr | Gly | Val | Leu | Thr | Pro | |
| 695 | | | | | 700 | | | | | 705 | | | | | 710 | |

| AAG | GGC | CAG | GAG | TAT | GGC | GGC | TCC | GAG | ATC | CGC | CCC | GAG | GCC | ACC | GGC | 720 |
|---|---|---|---|---|---|---|---|---|---|---|---|---|---|---|---|---|
| Lys | Gly | Gln | Glu | Tyr | Gly | Gly | Ser | Glu | Ile | Arg | Pro | Glu | Ala | Thr | Gly | |
| | | | | 715 | | | | | 720 | | | | | 725 | | |

| TAC | GGC | GCC | GTG | CTG | TTT | GTG | GAG | AAC | GTG | CTG | AAG | GAC | AAG | GGC | GAG | 768 |
|---|---|---|---|---|---|---|---|---|---|---|---|---|---|---|---|---|
| Tyr | Gly | Ala | Val | Leu | Phe | Val | Glu | Asn | Val | Leu | Lys | Asp | Lys | Gly | Glu | |
| | | | 730 | | | | | 735 | | | | | 740 | | | |

| AGC | CTC | AAG | GGC | AAG | CGC | TGC | CTG | GTG | TCT | GGC | GCG | GGC | AAC | GTG | GCC | 816 |
|---|---|---|---|---|---|---|---|---|---|---|---|---|---|---|---|---|
| Ser | Leu | Lys | Gly | Lys | Arg | Cys | Leu | Val | Ser | Gly | Ala | Gly | Asn | Val | Ala | |
| | | 745 | | | | | 750 | | | | | 755 | | | | |

| CAG | TAC | TGC | GCG | GAG | CTG | CTG | CTG | GAG | AAG | GGC | GCC | ATC | GTG | CTG | TCG | 864 |
|---|---|---|---|---|---|---|---|---|---|---|---|---|---|---|---|---|
| Gln | Tyr | Cys | Ala | Glu | Leu | Leu | Leu | Glu | Lys | Gly | Ala | Ile | Val | Leu | Ser | |
| 760 | | | | | 765 | | | | | 770 | | | | | | |

| CTG | TCC | GAC | TCC | CAG | GGC | TAC | GTG | TAC | GAG | CCC | AAC | GGC | TTC | ACG | CGC | 912 |
|---|---|---|---|---|---|---|---|---|---|---|---|---|---|---|---|---|
| Leu | Ser | Asp | Ser | Gln | Gly | Tyr | Val | Tyr | Glu | Pro | Asn | Gly | Phe | Thr | Arg | |
| 775 | | | | | 780 | | | | | 785 | | | | | 790 | |

| GAG | CAG | CTG | CAG | GCG | GTG | CAG | GAC | ATG | AAG | AAG | AAG | AAC | AAC | AGC | GCC | 960 |
|---|---|---|---|---|---|---|---|---|---|---|---|---|---|---|---|---|
| Glu | Gln | Leu | Gln | Ala | Val | Gln | Asp | Met | Lys | Lys | Lys | Asn | Asn | Ser | Ala | |
| | | | | 795 | | | | | 800 | | | | | 805 | | |

| CGC | ATC | TCC | GAG | TAC | AAG | AGC | GAC | ACC | GCC | GTG | TAT | GTG | GGC | GAC | CGC | 1008 |
|---|---|---|---|---|---|---|---|---|---|---|---|---|---|---|---|---|
| Arg | Ile | Ser | Glu | Tyr | Lys | Ser | Asp | Thr | Ala | Val | Tyr | Val | Gly | Asp | Arg | |
| | | 810 | | | | | 815 | | | | | 820 | | | | |

| CGC | AAG | CCT | TGG | GAG | CTG | GAC | TGC | CAG | GTG | GAC | ATC | GCC | TTC | CCC | TGC | 1056 |
|---|---|---|---|---|---|---|---|---|---|---|---|---|---|---|---|---|
| Arg | Lys | Pro | Trp | Glu | Leu | Asp | Cys | Gln | Val | Asp | Ile | Ala | Phe | Pro | Cys | |
| | | 825 | | | | | 830 | | | | | 835 | | | | |

| GCC | ACC | CAG | AAC | GAG | ATC | GAT | GAG | CAC | GAC | GCC | GAG | CTG | CTG | ATC | AAG | 1104 |
|---|---|---|---|---|---|---|---|---|---|---|---|---|---|---|---|---|
| Ala | Thr | Gln | Asn | Glu | Ile | Asp | Glu | His | Asp | Ala | Glu | Leu | Leu | Ile | Lys | |
| | 840 | | | | | 845 | | | | | 850 | | | | | |

| CAC | GGC | TGC | CAG | TAC | GTG | GTG | GAG | GGC | GCC | AAC | ATG | CCC | TCC | ACC | AAC | 1152 |
|---|---|---|---|---|---|---|---|---|---|---|---|---|---|---|---|---|
| His | Gly | Cys | Gln | Tyr | Val | Val | Glu | Gly | Ala | Asn | Met | Pro | Ser | Thr | Asn | |
| 855 | | | | | 860 | | | | | 865 | | | | | 870 | |

| GAG | GCC | ATC | CAC | AAG | TAC | AAC | AAG | GCC | GGC | ATC | ATC | TAC | TGC | CCC | GGC | 1200 |
|---|---|---|---|---|---|---|---|---|---|---|---|---|---|---|---|---|
| Glu | Ala | Ile | His | Lys | Tyr | Asn | Lys | Ala | Gly | Ile | Ile | Tyr | Cys | Pro | Gly | |
| | | | 875 | | | | | 880 | | | | | 885 | | | |

| AAG | GCG | GCC | AAC | GCC | GGC | GGC | GTG | GCG | GTC | AGC | GGC | CTG | GAG | ATG | ACC | 1248 |
|---|---|---|---|---|---|---|---|---|---|---|---|---|---|---|---|---|
| Lys | Ala | Ala | Asn | Ala | Gly | Gly | Val | Ala | Val | Ser | Gly | Leu | Glu | Met | Thr | |
| | | 890 | | | | | 895 | | | | | 900 | | | | |

| CAG | AAC | CGC | ATG | AGC | CTG | AAC | TGG | ACT | CGC | GAG | GAG | GTT | CGC | GAC | AAG | 1296 |
|---|---|---|---|---|---|---|---|---|---|---|---|---|---|---|---|---|
| Gln | Asn | Arg | Met | Ser | Leu | Asn | Trp | Thr | Arg | Glu | Glu | Val | Arg | Asp | Lys | |
| | | 905 | | | | | 910 | | | | | 915 | | | | |

| CTG | GAG | CGC | ATC | ATG | AAG | GAC | ATC | TAC | GAC | TCC | GCC | ATG | GGG | CCG | TCC | 1344 |

```
Leu Glu Arg Ile Met Lys Asp Ile Tyr Asp Ser Ala Met Gly Pro Ser
    920                 925                 930

CGC AGA TAC AAT GTT GAC CTG GCT GCG GGC GCC AAC ATC GCG GGC TTC    1392
Arg Arg Tyr Asn Val Asp Leu Ala Ala Gly Ala Asn Ile Ala Gly Phe
935                 940                 945                 950

ACC AAG GTG GCT GAT GCC GTC AAG GCC CAG GGC GCT GTT TAAGCTGCCC     1441
Thr Lys Val Ala Asp Ala Val Lys Ala Gln Gly Ala Val
                955                 960

AGGCCCAAGC CACGGCTCAC CGGCAATCCA AC                                1473
```

(2) INFORMATION FOR SEQ ID NO:26:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO:26:

```
Met Asp Ala Thr Thr Gly Asp Phe Thr Ala Leu Gln Lys Ala Val Lys
1               5                   10                  15

Gln Met Ala Thr Lys Ala Gly Thr Glu Gly Leu Val His Gly Ile Lys
                20                  25                  30

Asn Pro Asp Val Arg Gln Leu Leu Thr Glu Ile Phe Met Lys Asp Pro
            35                  40                  45

Glu Gln Gln Glu Phe Met Gln Ala Val Arg Glu Val Ala Val Ser Leu
        50                  55                  60

Gln Pro Val Phe Glu Lys Arg Pro Glu Leu Leu Pro Ile Phe Lys Gln
65                  70                  75                  80

Ile Val Glu Pro Glu Arg Val Ile Thr Phe Arg Val Ser Trp Leu Asp
                85                  90                  95

Asp Ala Gly Asn Leu Gln Val Asn Arg Gly Phe Arg Val Gln Tyr Ser
            100                 105                 110

Ser Ala Ile Gly Pro Tyr Lys Gly Gly Leu Arg Phe His Pro Ser Val
        115                 120                 125

Asn Leu Ser Ile Met Lys Phe Leu Ala Phe Glu Gln Ile Phe Lys Asn
130                 135                 140

Ser Leu Thr Thr Leu Pro Met Gly Gly Gly Lys Gly Gly Ser Asp Phe
145                 150                 155                 160

Asp Pro Lys Gly Lys Ser Asp Ala Glu Val Met Arg Phe Cys Gln Ser
                165                 170                 175

Phe Met Thr Glu Leu Gln Arg His Ile Ser Tyr Val Gln Asp Val Pro
            180                 185                 190

Ala Gly Asp Ile Gly Val Gly Ala Arg Glu Ile Gly Tyr Leu Phe Gly
        195                 200                 205

Gln Tyr Lys Arg Ile Thr Lys Asn Tyr Thr Gly Val Leu Thr Pro Lys
210                 215                 220

Gly Gln Glu Tyr Gly Gly Ser Glu Ile Arg Pro Glu Ala Thr Gly Tyr
225                 230                 235                 240

Gly Ala Val Leu Phe Val Glu Asn Val Leu Lys Asp Lys Gly Glu Ser
                245                 250                 255

Leu Lys Gly Lys Arg Cys Leu Val Ser Gly Ala Gly Asn Val Ala Gln
            260                 265                 270

Tyr Cys Ala Glu Leu Leu Leu Glu Lys Gly Ala Ile Val Leu Ser Leu
        275                 280                 285

Ser Asp Ser Gln Gly Tyr Val Tyr Glu Pro Asn Gly Phe Thr Arg Glu
```

-continued

```
                 290                     295                   300

Gln Leu Gln Ala Val Gln Asp Met Lys Lys Lys Asn Asn Ser Ala Arg
305                     310                 315                 320

Ile Ser Glu Tyr Lys Ser Asp Thr Ala Val Tyr Val Gly Asp Arg Arg
                325                     330                 335

Lys Pro Trp Glu Leu Asp Cys Gln Val Asp Ile Ala Phe Pro Cys Ala
                340                     345                 350

Thr Gln Asn Glu Ile Asp Glu His Asp Ala Glu Leu Leu Ile Lys His
                355                     360                 365

Gly Cys Gln Tyr Val Val Glu Gly Ala Asn Met Pro Ser Thr Asn Glu
        370                     375                 380

Ala Ile His Lys Tyr Asn Lys Ala Gly Ile Ile Tyr Cys Pro Gly Lys
385                     390                     395                 400

Ala Ala Asn Ala Gly Gly Val Ala Val Ser Gly Leu Glu Met Thr Gln
                405                     410                 415

Asn Arg Met Ser Leu Asn Trp Thr Arg Glu Glu Val Arg Asp Lys Leu
                420                     425                 430

Glu Arg Ile Met Lys Asp Ile Tyr Asp Ser Ala Met Gly Pro Ser Arg
        435                     440                 445

Arg Tyr Asn Val Asp Leu Ala Ala Gly Ala Asn Ile Ala Gly Phe Thr
        450                     455                 460

Lys Val Ala Asp Ala Val Lys Ala Gln Gly Ala Val
465                     470                 475
```